(12) United States Patent
Kitagawa et al.

(10) Patent No.: US 9,103,807 B2
(45) Date of Patent: Aug. 11, 2015

(54) RACK COLLECTING UNIT AND SAMPLE PROCESSING APPARATUS

(75) Inventors: Nobuhiro Kitagawa, Akashi (JP); Yuichiro Ohmae, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 401 days.

(21) Appl. No.: 12/883,633

(22) Filed: Sep. 16, 2010

(65) Prior Publication Data

US 2011/0076194 A1      Mar. 31, 2011

(30) Foreign Application Priority Data

Sep. 30, 2009    (JP) ................................ 2009-228312

(51) Int. Cl.
| | |
|---|---|
| *G01N 31/00* | (2006.01) |
| *G01N 35/00* | (2006.01) |
| *G01N 35/02* | (2006.01) |
| *G01N 35/04* | (2006.01) |
| G01N 21/00 | (2006.01) |
| G01N 33/00 | (2006.01) |
| B65D 37/00 | (2006.01) |

(52) U.S. Cl.
CPC .......... *G01N 35/026* (2013.01); *G01N 35/0092* (2013.01); *G01N 2035/00326* (2013.01); *G01N 2035/0401* (2013.01); *G01N 2035/0405* (2013.01); *G01N 2035/0415* (2013.01); *G01N 2035/0424* (2013.01); *G01N 2035/0465* (2013.01); *G01N 2035/0467* (2013.01)

(58) Field of Classification Search
USPC .......................... 422/63–67, 68.1; 436/43, 47
See application file for complete search history.

(56) References Cited

U.S. PATENT DOCUMENTS

| 5,232,081 | A | 8/1993 | Kanamori | |
|---|---|---|---|---|
| 5,972,295 | A * | 10/1999 | Hanawa et al. | ................. 422/65 |
| 6,599,749 | B1 * | 7/2003 | Kodama et al. | ................. 436/47 |
| 2004/0208787 | A1 * | 10/2004 | Takahashi et al. | .............. 422/64 |
| 2005/0287039 | A1 * | 12/2005 | Matsubara et al. | .......... 422/68.1 |
| 2007/0172396 | A1 * | 7/2007 | Neeper et al. | ................. 422/104 |
| 2007/0202011 | A1 * | 8/2007 | Nogawa et al. | ................. 422/65 |

FOREIGN PATENT DOCUMENTS

JP        2008032652 A  *  2/2008

* cited by examiner

*Primary Examiner* — Jennifer Wecker
(74) *Attorney, Agent, or Firm* — Brinks Gilson & Lione

(57) ABSTRACT

A rack collecting unit including: a transport path capable of transporting a sample rack in a first direction; a transport path capable of transporting the sample rack in a second direction opposite to the first direction; a storing section for storing therein the sample rack; and a transferring section for transferring the sample rack carried onto the transport paths to the storing section.

16 Claims, 22 Drawing Sheets

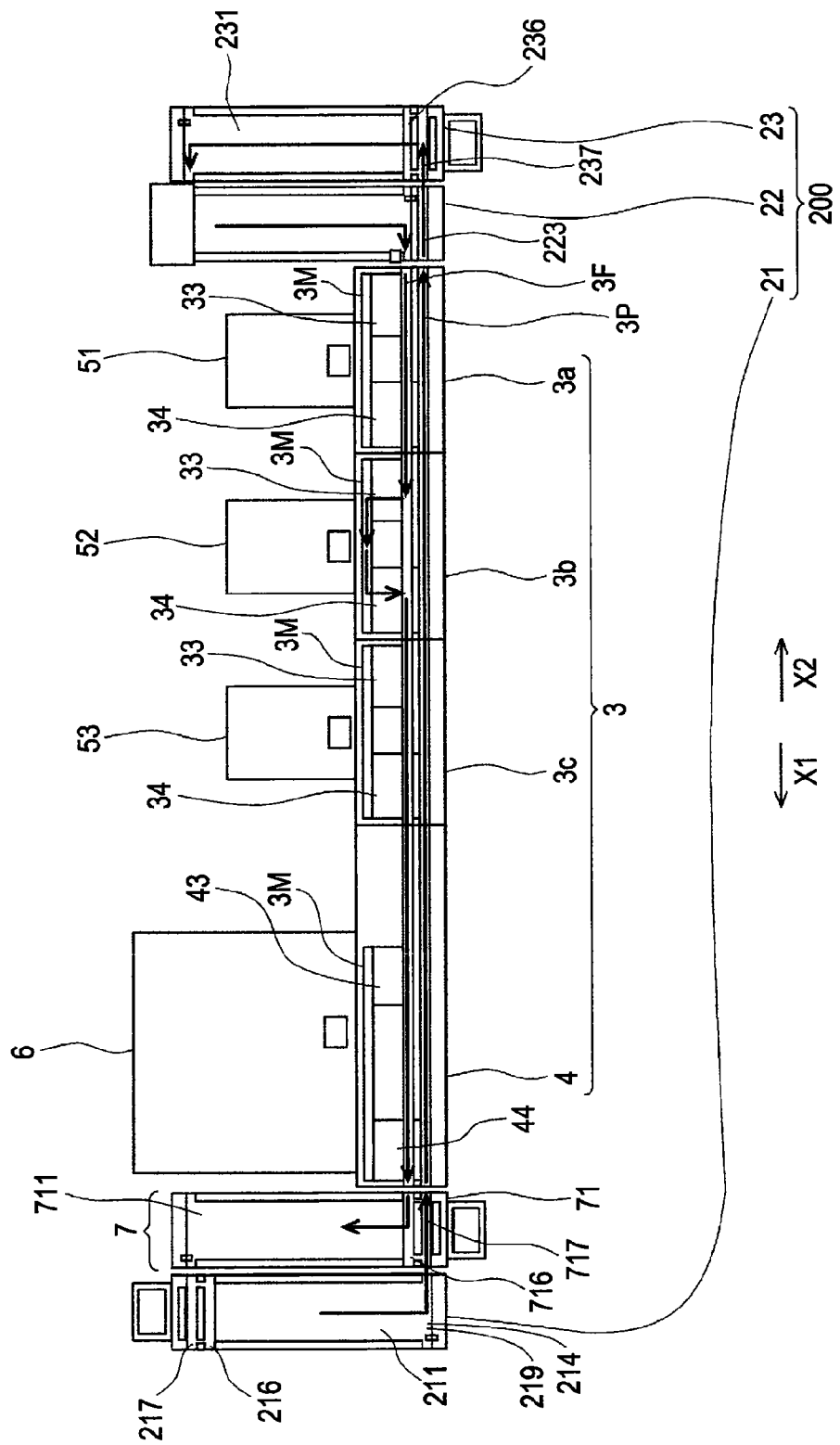

RACK COLLECTING UNIT AND SAMPLE PROCESSING APPARATUS

RELATED APPLICATIONS

This application claims priority under 35 U.S.C. §119 to Japanese Patent Application No. 2009-228312 filed on Sep. 30, 2009, the entire content of which is hereby incorporated by reference.

BACKGROUND OF THE INVENTION

1. Field of the Invention

The present invention relates to a rack collecting unit for collecting a sample rack, and a sample processing apparatus equipped with the rack collecting unit.

2. Description of the Related Arts

For example, U.S. Pat. No. 5,232,081 discloses a conventional sample processing system, having a rack setting unit for sending out a sample rack set by a user, a transport unit for transporting the sample rack sent out from the rack setting unit, a sample processing unit for performing processing of a sample contained in the sample rack transported by the transport unit, for example, analyzing the sample or preparing a smear slide from the sample, and a rack collecting unit for collecting the sample rack transported by the transport unit.

A sample analyzing system provided with an analyzing apparatus, a transferring section, a rack setting section, and a rack collecting section is disclosed in the above U.S. Pat. No. 5,232,081. In the sample analyzing system, the rack setting section is provided on the right side of the transferring section, and the rack collecting section is provided on the left side of the transferring section. The rack setting section sends out sample racks one by one to the transferring section. The transferring section is connected to the analyzing apparatus, and transfers the sample rack from the upstream side to downstream side. The samples thus transferred are analyzed by the analyzing apparatus, and the sample rack holding the analyzed samples is transferred by the transferring section to the rack collecting section to be thereby collected. In the rack setting section and the rack collecting section of the sample analyzing system, a first rack setting/collecting unit and a second rack setting/collecting unit are connected in turns. Each of the first and second rack setting/collecting units includes a fetching section for fetching the sample rack from outside and transporting the fetched sample rack in a predetermined direction, a storing section for receiving the sample rack from the fetching section and storing the received sample rack therein, and a delivering section for transporting the sample rack received from the storing section in the predetermined direction to deliver the sample rack outside. In the rack setting section and the rack collecting section, the first and second rack setting/collecting units are connected so that the fetching section of the first rack setting/collecting unit and the delivering section of the second rack setting/collecting unit are in communication with each other.

The sample processing system as described above is installed in such a facility as a hospital or an inspection center. In this case, depending on the configuration of installation location of the sample processing system in the facility, the system may have to flexibly accommodate different requests for the arrangement position of the rack collecting unit or the rack setting unit, for example, provide the rack collecting unit away from the rack setting unit, or provide the rack collecting unit near the rack setting unit. In the sample analyzing system recited in U.S. Pat. No. 5,232,081, while the number of the rack setting/collecting units to be provided in the rack setting section and the rack collecting section can be easily increased, it was not possible to flexibly change the arrangement position of the rack collecting section or the rack setting section such as providing the rack collecting section near the rack setting section.

The scope of the present invention is defined solely by the appended claims, and is not affected to any degree by the statements within this summary.

A first aspect of the present invention is a rack collecting unit usable in a first sample processing apparatus and a second sample processing apparatus, wherein the first sample processing apparatus transports a sample rack sent out from a rack setting unit to a rack collecting unit through a sample processing unit using a first transport path for transporting the sample rack in a first direction, and the second sample processing apparatus transports the sample rack sent out from the rack setting unit to a sample processing unit using a first transport path for transporting the sample rack in the first direction and thereafter transports the sample rack to the rack collecting unit using a second transport path for transporting the sample rack in a second direction opposite to the first direction, the rack collecting unit comprising:

a third transport path connectable to the first transport path and capable of transporting the sample rack in the first direction;

a fourth transport path connectable to the second transport path and capable of transporting the sample rack in the second direction;

a storing section for storing therein the sample rack; and a transferring section for transferring the sample rack carried onto the third transport path or the fourth transport path to the storing section.

A second aspect of the present invention is a sample processing apparatus, comprising: a rack setting unit, on which a sample rack holding a sample container is set by a user, and which sends out the sample rack; a transport unit having one end side connected to the rack setting unit, the transport unit including a first transport path for transporting the sample rack sent out from the rack setting unit in a first direction, and a second transport path for transporting the sample rack in a second direction opposite to the first direction; a sample processing unit for processing a sample in the sampler container held by the sample rack transported by the first transport path of the transport unit; and a rack collecting unit for collecting the sample rack transported by the transport unit, wherein the rack collecting unit comprises: a third transport path connectable to the first transport path and capable of transporting the sample rack in the first direction; a fourth transport path connectable to the second transport path and capable of transporting the sample rack in the second direction; a storing section for storing therein the sample rack; and a transferring section for transferring the sample rack carried onto the third transport path or the fourth transport path to the storing section, and wherein the rack collecting unit is connectable to the other end side of the transport unit and the rack setting unit.

BRIEF DESCRIPTION OF THE DRAWINGS

FIG. 21 is a schematic view for describing sample rack transport paths of the sample processing system in the fifth layout example according to the embodiment.

DETAILED DESCRIPTION OF THE PREFERRED EMBODIMENTS

Figure 1:
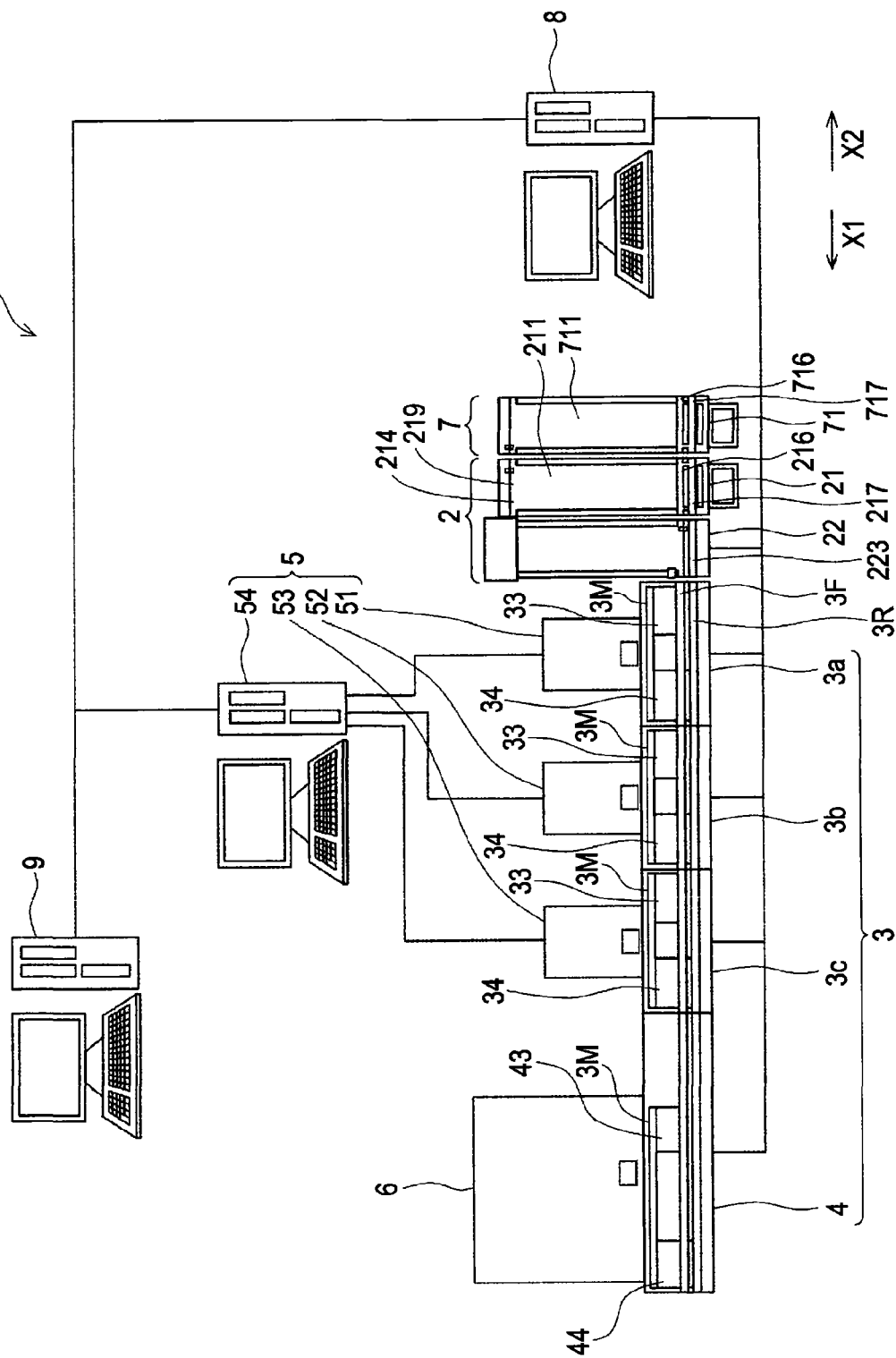
FIG. 1 is a schematic plan view illustrating an overall structure of a sample processing system in a first layout example according to an embodiment of the present invention.

Hereinafter, a preferred embodiment of the present invention is described referring to the drawings.

First Layout Example of Sample Processing System

FIG. 1 is a schematic plan view illustrating an overall structure of a sample processing system in a first layout example according to an embodiment of the present invention. As illustrated in FIG. 1, a sample processing system 1 is equipped with a sample setting apparatus 2, a sample transporting apparatus 3, a hemocyte analyzing apparatus 5, a smear preparation apparatus 6, a sample collecting apparatus 7, and a system control apparatus 8. The sample processing system 1 according to the present embodiment is connected to a test information management apparatus 9 through a communication network to enable data communication therebetween.

The sample transporting apparatus 3 has sample transport units 3a, 3b, 3c, and 4. These sample transport units 3a, 3b, 3c, and 4 are linearly connected to one another in such a manner that they extend laterally in the drawing. The blood analyzing apparatus 5 has three measurement units 51, 52, and 53, and an information processing unit 54. The measurement unit 51 is provided behind the sample transport unit 3a, the measurement unit 52 is provided behind the sample transport unit 3b, and the measurement unit 53 is provided behind the sample transport unit 3c. The smear preparation apparatus 6 is provided behind the sample transport unit 4.

In the sample transporting apparatus 3, all of the sample transport units 3a, 3b, 3c, and 4 are provided laterally in a linear manner. The sample transporting apparatus 3 is provided with a transport line 3F for transporting a sample rack holding a plurality of samples leftward in the drawing, and a return line 3R disposed in parallel with the transport line 3F and for transporting the sample rack rightward in the drawing. Each of the sample transport units 3a, 3b, 3c, and 4 is provided with a measurement line 3M extending leftward and rightward which transports a sample rack L to supply samples contained therein to the measurement units 51, 52, and 53, and the smear preparation apparatus 6. Between the transport line 3F and each of the measurement lines 3M, there are pre-analysis rack holding sections 33 and 43 which are transfer paths for transferring the sample rack from the transport line 3F to a starting point of the measurement line 3M and also regions for holding the sample rack, and post-analysis rack holding sections 34 and 44 which are transfer paths for transferring the sample rack from an end point of the measurement line 3M to the transport line 3F or the return line 3R and also regions for holding the sample rack.

The sample setting apparatus 2 provided to send out the sample rack set by the user is connected to the right end of the sample transporting apparatus 3 to transport the sample rack sent out by the sample setting apparatus 2 using the transport line 3F of the sample transporting apparatus 3. The sample collecting apparatus 7 provided to collect the sample rack is connected to the sample setting apparatus 2 in the first layout example. The sample rack is transferred from the transport line 3F to the measurement line 3M through the pre-analysis rack holding section 33 or the pre-process rack holding section 43 in the sample transport unit 3a, 3b, 3c, or 4 corresponding to the measurement unit 51, 52 or 53, or the smear preparation apparatus 6 which is a destination of the transported sample rack. The sample rack is transported on the measurement line 3M to be supplied to its destination, which is the measurement unit 51, 52 or 53, or the smear preparation apparatus 6. In the first layout example, the sample is supplied to the measurement unit 51, 52 or 53, or the smear preparation apparatus 6. Then, the sample rack L is transferred from the measurement line 3M to the return line 3R through the post-analysis rack holding section 34 or the post-process rack holding section 44, and transported rightward from the return line 3R to be collected by the sample collecting apparatus 7 by way of the sample setting apparatus 2.

The sample collecting apparatus 7 can be separated from the sample setting apparatus 2. The sample collecting apparatus 7 can be connected to the left end of the sample transporting apparatus 3. In this manner, the location of the sample collecting apparatus 7 according to the present embodiment can be thus changed. The sample collecting apparatus 7 can be provided at any suitable positions in different facilities. Hereinafter, the structure of the sample processing system 1 is described in detail.

<Structures of Sample Setting Apparatus 2 and Sample Collecting Apparatus 7>

Figure 2:
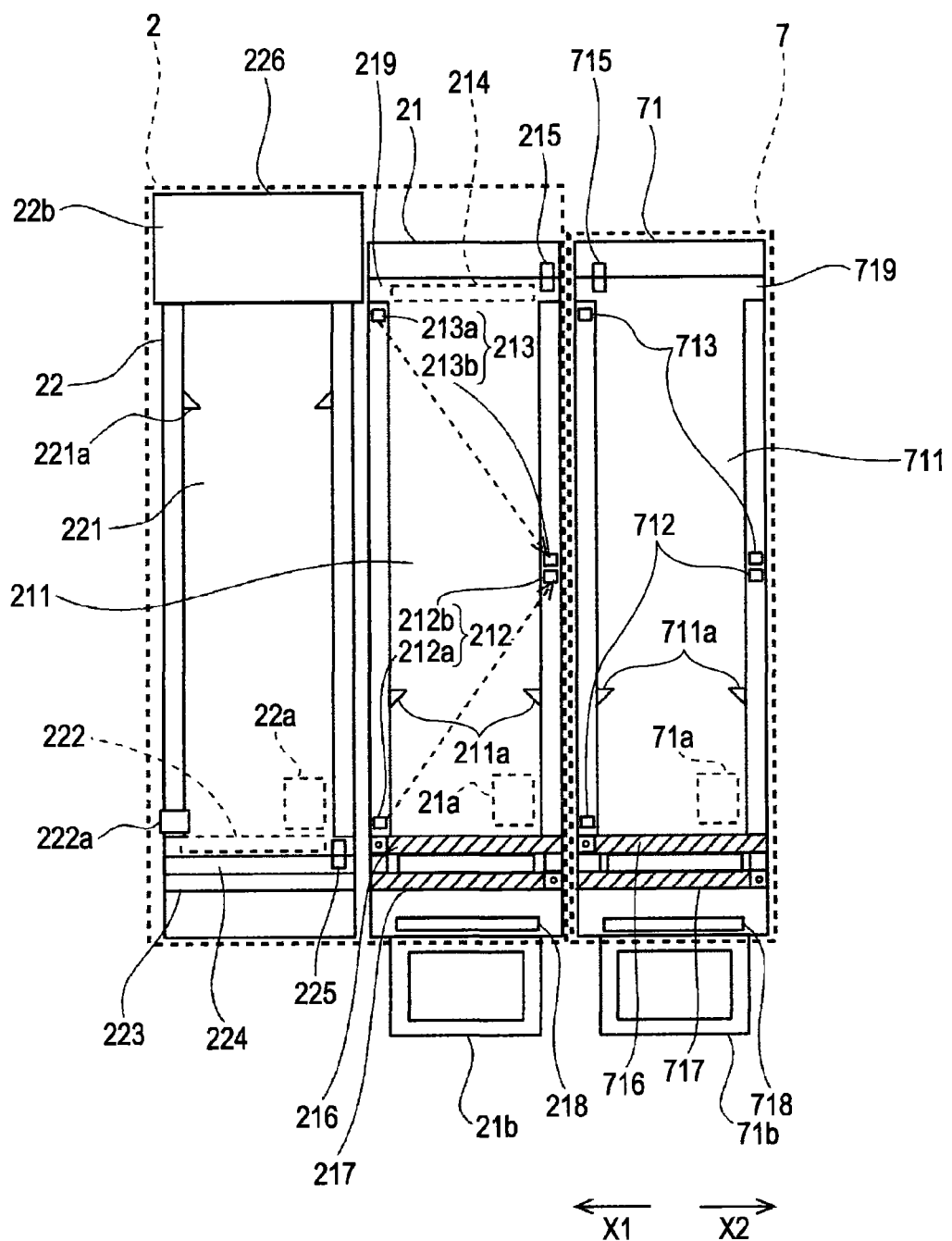
FIG. 2 is a plan view illustrating structures of a sample setting apparatus and a sample collecting apparatus according to the embodiment.

FIG. 2 is a plan view illustrating structures of the sample setting apparatus and the sample collecting apparatus according to the present embodiment. The sample setting apparatus 2 has a rack setting unit 21 and a pre-processing unit 22. The sample setting apparatus 2 has a structure where a plurality of sample racks holding a plurality of sample containers can be set by the user. The sample collecting apparatus 7 is connected to the rack setting unit 21 of the sample setting apparatus 2 having such a structure. The sample collecting apparatus 7 according to the present embodiment is equipped with one rack collecting unit 71.

Figure 3:
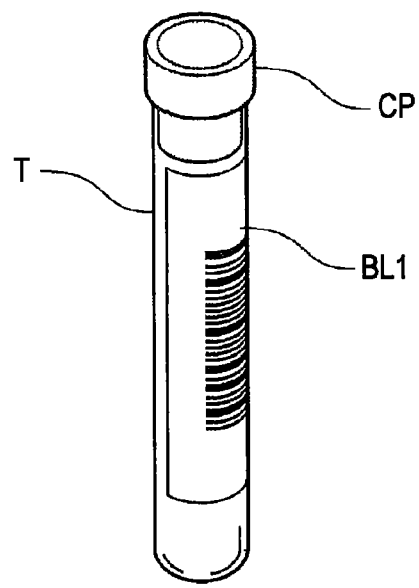
FIG. 3 is a perspective view illustrating an external appearance of a sample container.
Figure 4:
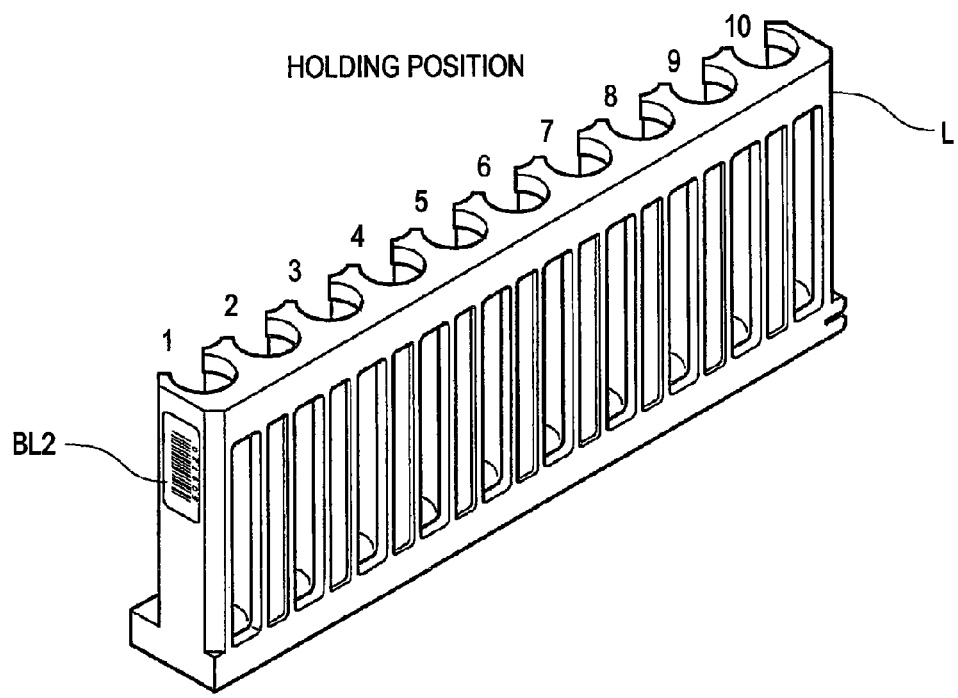
FIG. 4 is a perspective view illustrating an external appearance of a sample rack.

FIG. 3 is a perspective view illustrating an external appearance of the sample container, and FIG. 4 is a perspective view illustrating an external appearance of the sample rack. As illustrated in FIG. 3, a sample container T has a tubular shape having an open upper end. A sample which is blood collected from a patient is held in the sample container, and the open upper end is sealed with a cap portion CP. The sample container T is made of translucent glass or synthetic resin so that the blood sample inside can be visually confirmed. A barcode label BL1 is affixed to a side surface of the sample container T. The barcode label BL1 has a barcode representing a sample ID (sample barcode) printed thereon. The sample rack L can hold 10 sample containers T in an aligned manner. The sample rack L holds the sample containers T perpendicularly (in upright position). A barcode label BL2 is affixed to a side surface of the sample rack L. The barcode label BL2 has a barcode representing a rack ID (rack barcode) printed thereon.

Figure 5A:
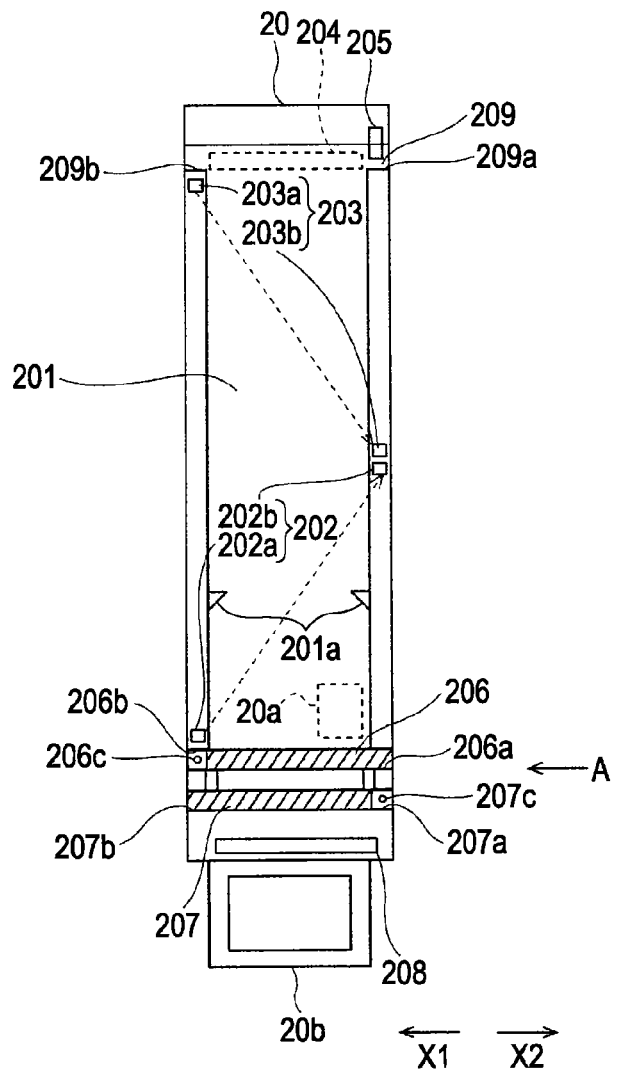
FIG. 5A is a plan view illustrating a structure of a shared unit according to the embodiment.
Figure 5B:
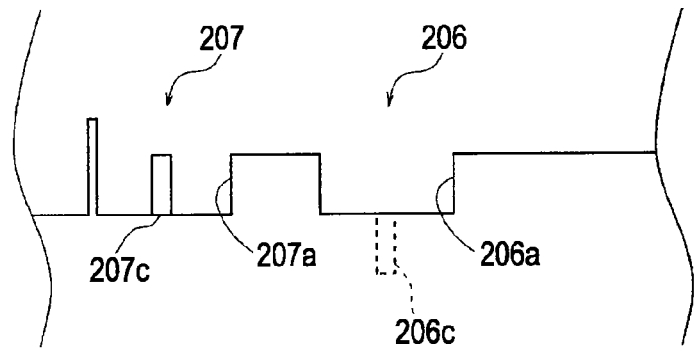
FIG. 5B is an enlarged side view illustrating a first transport path and a second transport path of the shared unit according to the embodiment when they are viewed in the direction of arrow A.

The rack setting unit 21 and the rack collecting unit 71 have an identical structure. FIG. 5A is a plan view illustrating a structure of a shared unit 20 used as the rack setting unit 21 and the rack collecting unit 71. FIG. 5B is an enlarged side view illustrating a first transport path 206 and a second transport path 207 of the shared unit 20 when they are viewed in the direction of arrow A. The shared unit 20 has a rack housing section 201 formed in the shape of a recess to house therein the sample rack L holding the sample containers T. The rack housing section 201 has a rectangular shape, where a plurality of sample racks L can be housed at a time. The sample rack L is housed in the rack housing section 201 so that the sample containers T are transversely aligned. The rack housing section 201 is provided with sensors 202 and 203 for detecting the sample rack L, and engagement portions 201a for transferring the sample rack L. The sensors 202 and 203 are optical sensors. The sensor 202 has a light emitter 202a and a light receiver 202b, and the sensor 203 has a light emitter 203a and a light receiver 203b. The light emitter 202a is provided at a position on the forward left side of the rack housing section 201, and the light receiver 202b is provided at a center position on the right side of the rack housing section 201. The light emitter 203a is provided at a position on the rearward left side of the rack housing section 201, and the light emitter 203b is provided at a center position on the right side of the rack housing section 201. The light emitter 202a is positioned to emit light diagonally backward right, and the light receiver 202b is positioned to receive the emitted light passing across the rack housing section 201. The light emitter 203a is positioned to emit light diagonally forward right, and the light receiver 203b is positioned to receive the emitted light passing across the rack housing section 201. Accordingly, the light emitted from the light emitter 202a or 203a is blocked by the sample rack L housed in the rack housing section 201, and the light receiving capacity of the light receiver 202b or 203b is thereby lowered. As a result, the sample rack L is detected by the rack sensor 202 or 203. The sample rack L detected by the rack sensor 202 or 203 is engaged with the engagement portions 201a, and the sample rack L is transported backward with the engagement portions 201a engaged therewith. Thus, the sample rack L is transferred on the rack housing section 201.

A third transport path 209 for transporting the sample rack leftward is provided on the rearmost side (rearward) of the rack housing section 201. The third transport path 209 has a protruding portion 205 movable rightward and leftward. The protruding portion 205 remains standby at a position near the right end of a rack delivering position 204 until the sample rack L is transferred to the rack delivering position 204. After the sample rack L arrives at the rack delivering position 204, the protruding portion 205 moves leftward. The sample rack L is pushed by the protruding portion 205 to be transferred leftward. The rack delivering position 204 has a structure where walls on the right and left sides are removed. The structure of the rack delivering position 204 provides an opening 209a and an opening 209b at the right and left end portions of the third transport path. Therefore, the sample rack L pushed by the protruding portion 205 is delivered to outside from the shared unit 20.

The first transport path 206 and the second transport path 207, which are transport paths in parallel with each other, are provided on the front side of the rack housing section 201. The walls surrounding the rack housing section 201 of the shared unit 20 have such a shape that part of the walls on the right and left sides of the first transport path 206 and the second transport path 207 is removed, thereby forming openings 206a and 206b and openings 207a and 207b at the both end portions of the first transport path 206 and the second transport path 207. Accordingly, the sample rack L can be transported to the first transport path 206 and the second transport path 207, and then transported from the first transport path 206 and the second transport path 207 to any different unit. Each of the first transport path 206 and the second transport path 207 includes an annular belt (hatched parts) and a belt conveyer having a motor which rotates the belt. The first transport path 206 transports the sample rack L in the direction of X1 (leftward), and the second transport path 207 transports the sample rack L in the direction of X2 (rightward). The first transport path 206 and the second transport path 207 can transport the sample rack in the directions of X1 and X2 both. A stopper 206c which may protrude through an upper surface of the first transport path 206 is provided at the left end portion of the first transport path 206. To stop the sample rack L transported to the first transport path 206 on the first transport path 206, the stopper 206c sticks out through the upper surface of the first transport path 206. To let the sample rack L transported to the first transport path 206 pass in the direction of X1, the stopper 206c drops downward below the upper surface of the first transport path 206. A stopper 207c which may protrude through an upper surface of the second transport path 207 is provided at the right end portion of the second transport path 207. To stop the sample rack L transported to the second transport path 207 on the second transport path 207, the stopper 207c sticks out through the upper surface of the second transport path 207. To let the sample rack L transported to the second transport path 207 pass in the direction of X2, the stopper 207c drops downward below the upper surface of the second transport path 207. In the illustration of FIG. 5B, the stopper 206c of the first transport path 206 is below its upper surface, and the stopper 207c of the second transport path 207 sticks out upward.

The upper surfaces of the rack housing section 201, first transport path 206, and second transport path 207 have an equal height, thereby forming a substantially flat and continuous plane. The shared unit 20 is provided with a rack transferring section 208 for transferring the sample rack L transported to the first transport path 206 or the second transport path 207 backward. The rack transferring section 208 has the shape of a laterally long bar. The rack transferring section 208 is movable forward and backward in an area from the second transport path 207 to an intermediate position in the longitudinal direction of the rack housing section 201. When the rack transferring section 208 on the front side of the sample rack L transported to the first transport path 206 or the second transport path 207 moves backward, the rack transferring section 208 abuts on the front surface of the sample rack L. When the rack transferring section 208 moves further backward, the sample rack L is thereby pushed backward. Then, the sample rack L is transferred backward to reach a position beyond the engagement portions 201a, so that the engagement portions 201a can transfer the sample rack L to the rack delivering position 204. Thus, the shared unit 20 can transport the sample rack L transported to the first transport path 206 to the apparatus on the left side and can also deliver the sample rack L transported to the second transport path 207 to the apparatus on the right side. The shared unit 20 is also able to transfer the sample rack L on the first transport path 206 or the second transport path 207 to the rack housing section 201, and transfer the sample rack L housed in the rack housing section 201 to the rack delivering position 204 and then deliver the sample rack L to the apparatus on the left side.

The shared unit 20 having the structure described above includes a controller 20a having, for example, a CPU and a memory. The controller 20a controls the mechanism of the shared unit 20. The shared unit 20 is equipped with an Ethernet (registered trademark) interface, and can be connected to other apparatuses (information processing unit 54 and system control apparatus 8) through LAN to communicate with these apparatuses. The shared unit 20 is provided with an operation panel 20b. A user can input instructions to the shared unit 20 by operating the operation panel 20b.

The rack housing section 201 of the shared unit 20, which is used as the rack setting unit 21, also serves as a rack loading section 211 where the sample rack L is loaded by the user. Similarly, the engagement portions 201a of the shared unit 20 used as the rack setting unit 21 serve as engagement portions 211a, the sensors 202 and 203 serve as sensors 212 and 213, the protruding portion 205 serves as a protruding portion 215, the first transport path 206 and the second transport path 207 serve as a first transport path 216 and a second transport path 217, the third transport path 209 serves as a third transport path 219, the rack transferring section 208 serves as a rack transferring section 218, and the controller 20a serves as a controller 21a.

The rack housing section 201 of the shared unit 20, which is used as the rack collecting unit 71, also serves as a rack storing section 711 for storing the collected sample rack L. Similarly, the engagement portions 201a of the shared unit 20 used as the rack setting unit 71 serve as engagement portions 711a, the sensors 202 and 203 serve as sensors 712 and 713, the protruding portion 205 serves as a protruding portion 715, the first transport path 206 and the second transport path 207 serve as a first transport path 716 and a second transport path 717, the third transport path 209 serves as a third transport path 719, the rack transferring section 208 serves as a rack transferring section 718, and the controller 20a serves as a controller 71a.

In the first layout example, the rack collecting unit 71 is connected to the right side of the rack setting unit 21. The rack setting unit 21 and the rack collecting unit 71 are positioned so that the first transport path 216 of the rack setting unit 21 and the first transport path 716 of the rack collecting unit 71 are linearly continuous, and the second transport path 217 of the rack setting unit 21 and the second transport path 717 of the rack collecting unit 71 are linearly continuous.

The pre-processing unit 22 is connected to the left side of the rack setting unit 21. The sample rack L delivered leftward from a rack delivering position 214 (corresponding to the rack delivering position 204 of the shared unit 20) is transported into the pre-processing unit 22. The pre-processing unit 22 is provided with a rack loading section 221 having a square shape in plane view and capable of housing a plurality of sample racks L. The pre-processing unit 22 is also provided with a barcode reader 22b on the rear side of the rack loading section 221. The barcode reader 22b can read at a time the sample barcodes of a plurality of sample containers T housed in the sample rack L, and further read at the same time the rack barcode of the sample rack L. The barcode reader 22b is equipped with an optical sensor for detecting the sample container T (not illustrated). When the sample rack L arrives at a position where the barcode is read by the barcode reader 22b, the optical sensor detects whether there is the sample container T therein. In the barcode reader 22b, a horizontal rotation mechanism (not illustrated) which horizontally rotates at a time a plurality of sample containers T is further provided immediately above the barcode reading position on the rearmost side of the rack loading section 221. The sample rack L delivered from the rack delivering position 214 of the rack setting unit 21 is transported leftward toward the pre-processing unit 22 and then arrives at the barcode reading position. After that, the sample container T housed in the sample rack L is horizontally rotated by the horizontal rotation mechanism. During the rotation, the sample ID is read from the barcode label BL1 by the barcode reader 22b, and the rack ID is read from the barcode label BL2 of the sample rack L.

Engagement portions 221a are protruding from the right and left walls of the rack loading section 221. The engagement portions 221a are engaged with the sample rack L from which the sample barcode and the rack barcode are already read by the barcode reader 22b, and then move forward. The movement transports the sample rack L forward on the rack loading section 221. A position on the frontmost side of the rack loading section 221 is a rack delivering position 222. On the front side of the rack delivering position 222, a transport path 223 for transporting the sample rack L is provided, and a partitioning section 224 formed in the shape of a wall is provided in a protruding manner between the transport path 223 and the rack delivering position 222. The partitioning section 224 is provided with a protruding portion 225 movable leftward and rightward. The protruding portion 225 remains standby at a position near the right end of the rack delivering position 222 until the sample rack L is transported to the rack delivering position 222. After the sample rack L arrives at the rack delivering position 222, the protruding portion 225 moves leftward. The sample rack L is pushed by the protruding portion 225 to be transported leftward. On the right and left sides of the rack delivering position 222, there are no walls. Therefore, the sample rack L pushed by the protruding portion 225 is delivered from the pre-processing unit 22. As illustrated in FIG. 1, the sample transporting apparatus 3 is connected to the left side of the pre-processing unit 22, and the rack delivering position 222 is linearly continuous to the transport line 3F of the sample transporting apparatus 3. According to this structure, the sample rack L delivered from the rack delivering position 222 is guided to the transport line of the sample transporting apparatus 3.

A barcode reader 222a used to read the rack barcode is provided near the rack delivering position 222. The rack ID of the sample rack L transported to the rack delivering position 222 is read by the barcode reader 222a, and the read rack ID is transmitted to the system control apparatus 8. As described later, the system control apparatus 8 receives the rack ID thus read and decides the destination of the sample rack L based on the received rack ID.

On the right and left side of the transport path 223, there are no walls. The transport path 223 thus formed is linearly continuous to the return line 3R of the sample transporting apparatus 3 described later and the second transport path 217 of the rack setting unit 21 described above. Accordingly, the transport path 223 receives the sample rack L from the return line 3R of the sample transporting apparatus 3, and transports the received sample rack L to the second transport path 217 of the rack setting unit 21.

The pre-processing unit 22 having the structure described above includes a controller 22a having, for example, a CPU and a memory. The controller 22a controls the mechanism of the pre-processing unit 22. The pre-processing unit 22 is equipped with an Ethernet (registered trademark) interface, and can be connected to the information processing unit 54 and the system control apparatus 8 through LAN to communicate with these apparatuses.

<Structure of Sample Transporting Apparatus 3>

A structure of the sample transporting apparatus 3 is described below. As illustrated in FIG. 1, the sample processing system 1 includes the sample transporting apparatus 3, provided with four sample transport units 3a, 3b, 3c, and 4. On the front side of the three measurement units 51, 52, and 53 of the hemocyte analyzing apparatus 5, there are provided the sample transport units 3a, 3b, and 3c which respectively deal with the measurement units. Of the sample transport units 3a, 3b, and 3c, the two sample transport units which are adjacently disposed are connected to each other so that the sample rack L is transported to and from the two units. The rightmost sample transport unit 3a is connected to the sample setting apparatus 2. The transport line 3F is linearly continuous to the rack delivering position 222 of the pre-processing unit 22, and the return line 3R is linearly continuous to the transport path 223 of the pre-processing unit 22. According to the structure, the sample rack L transported from the sample setting apparatus 2 can be guided to the transport line 3F, and then transported from the return line 3R to the sample setting apparatus 2.

The sample rack L transported from the sample setting apparatus 2 to the sample transporting apparatus 3 is transported by the transport line 3F leftward in the drawing. Following an instruction relating to the destination sent from the system control apparatus 8, the sample transporting apparatus 3 can temporarily keep the sample rack L transported on the transport line 3F in the pre-analysis rack holding section 33, 43, and later transfer the sample rack L to the measurement line 3M so that the sample rack L is transported to its destination, which is the measurement unit 51, 52, 53, or smear preparation apparatus 6. The sample transport unit 3a, 3b, 3c, or 4 can transfer the sample rack L, from which the sample is already supplied to the measurement unit 51, 52, 53, or smear preparation apparatus 6, from the end point of the measurement line 3M to the post-analysis rack holding section 34, 44 to temporarily keep the sample rack L there, and then transfer the sample rack L to the transport line 3F or the return line 3R. The sample rack L transferred to the transport line 3F is further transported along the transport line 3F toward the downstream side of the transport direction (leftward), and the sample rack L transferred to the return line 3R is transported along the return line 3R toward the upstream side of the transport direction (rightward).

<Structure of Hemocyte Analyzing Apparatus 5>

The hemocyte analyzing apparatus 5 is a multiple hemocyte analyzing apparatus which uses optical flow cytometry. A side scattered light intensity and a fluorescence intensity, for example, of hemocytes included in blood collected as a sample are obtained to classify types of the hemocytes included in the sample based on the obtained intensities. Further, the hemocytes of the different types are separately counted, and a scattergram in which the hemocytes thus classified are shown in different colors is created and displayed. The hemocyte analyzing apparatus 5 includes the measurement units 51, 52, and 53 which measure the blood sample, and the information processing unit 54 including a computer which processes measured data outputted from the measurement units 51, 52, and 53 and displays an analysis result of the blood sample.

As illustrated in FIG. 1, the hemocyte analyzing apparatus 5 includes three measurement units 51, 52, and 53 and one information processing unit 54. The information processing unit 54 is connected to the three measurement units 51, 52, and 53 to enable data communication therebetween. The information processing unit 54 can control the operations of the three measurement units 51, 52, and 53. The information processing unit 54 is also connected to three sample transport units 3a, 3b, and 3c respectively provided on the front side of the three measurement units 51, 52, and 53 to enable data communication therebetween.

Figure 6:
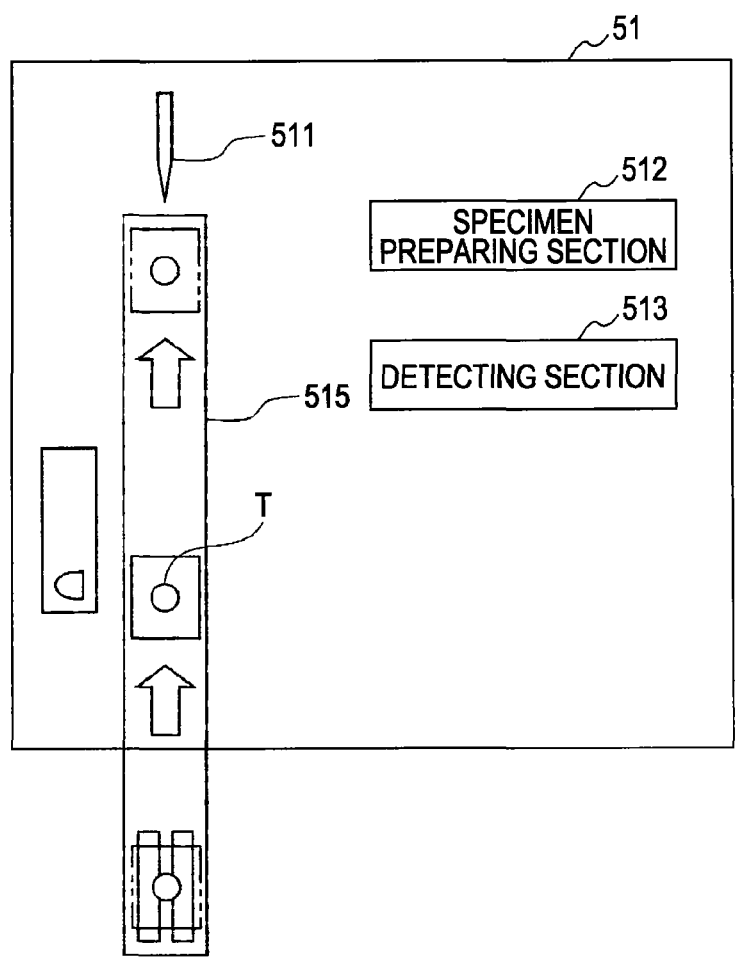
FIG. 6 is a block diagram illustrating a structure of a measurement unit provided in a blood analyzing apparatus according to the embodiment.

FIG. 6 is a block diagram illustrating a structure of the measurement unit 51. As illustrated in FIG. 6, the measurement unit 51 has a sample suctioning section 511 which suctions blood collected as a sample from the sample container (blood collecting tube) T, a specimen preparing section 512 which prepares a measurement specimen for measurement from the blood suctioned by the sample suctioning section 511, and a detecting section 513 which detects hemocytes from the measurement specimen prepared by the specimen preparing section 512. The measurement unit 51 further has a fetching port (not illustrated) through which the sample container T housed in the sample rack L transported by the measurement line 3M of the sample transport unit 3a is fetched inside, and a sample container transport section 515 which fetches the sample container T into the measurement unit 51 from the sample rack L and transports the fetched sample container T to a suctioning position where the sample is suctioned by the sample suctioning section 511.

The detecting section 513 is able to detect RBC (red blood cells) and PLT (platelets) by employing sheath flow DC detection. The detecting section 513 is able to detect HGB (hemoglobin) by employing SLS-hemoglobin method and detect WBC (white blood cells) by employing flow cytometry in which a semiconductor laser is used.

The measurement units 52 and 53 are structurally and functionally similar to the measurement unit 51, each including a sample suctioning section, a specimen preparing section, a detecting section, and a sample container transport section.

<Structure of Smear Preparation Apparatus 6>

To prepare a smear, the smear preparation apparatus 6 suctions the blood sample and drops the suctioned blood sample on a glass side, spreads the dropped blood sample on the glass slide very thin and dries the blood sample, and then supplies a staining liquid on the glass slide to stain the blood thereon.

Figure 7:
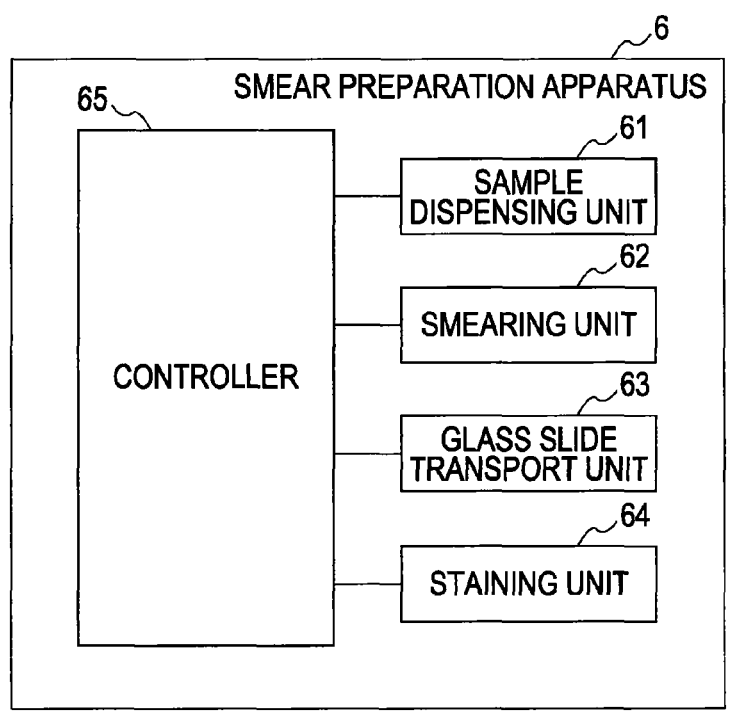
FIG. 7 is a block diagram illustrating a schematic structure of a smear preparation apparatus according to the embodiment.

FIG. 7 is a block diagram illustrating a schematic structure of the smear preparation apparatus 6. As illustrated in FIG. 7, the smear preparation apparatus 6 has a sample dispensing unit 61, a smearing unit 62, a glass slide transport unit 63, a staining unit 64, and a controller 65.

The sample dispensing unit 61 has a suctioning tube (not illustrated). The sample dispensing unit 61 penetrates the suctioning tube into the cap portion CP of the sample container T housed in the sample rack L transported on the measurement line 3M of the sample transport unit 4 to suction the blood sample from the sample container T. The sample dispensing unit 61 drops the suctioned blood sample on the glass slide. The smearing unit 62 smears the blood sample dropped on the glass side, and dries and prints the dropped blood sample on the glass slide.

The glass slide transport unit 63 is provided to house the glass slide on which the blood sample is smeared by the smearing unit 62 in a cassette (not illustrated), and transport the cassette. The staining unit 64 supplies the staining solution to the glass slide in the cassette transported to a staining position by the glass slide transport unit 63. The controller 65 controls the sample dispensing unit 61, smearing unit 62, glass slide transport unit 63, and staining unit 64 in accordance with a sample preparation instruction obtained from the sample transporting apparatus 3 to carry out the smear preparing operation described earlier.

<Structure of System Control Apparatus 8>

The system control apparatus 8 including a computer controls the overall operation of the sample processing system 1. The system control apparatus 8 receives a rack number affixed to the sample rack L from the sample setting apparatus 2 and decides the destination of the sample rack L, and then transmits a transport instruction data which instructs the transport of the sample rack L to the decided destination to the sample setting apparatus 2, sample transporting apparatus 3, and sample collecting apparatus 7.

<Structure of Test Information Management Apparatus 9>

The test information management apparatus 9 is an apparatus which manages information relating to tests performed in a facility, generally called LIS (Laboratory Information System), which is connected not only to the blood analyzing apparatus 5 but also to a clinical sample testing apparatus. The test information management apparatus 9 including a computer receives a measurement order inputted by an operator or transmitted from a device such as an electronic chart system, and stores and manages the received measurement order. Further, the test information management apparatus 9 receives an order request from the system control apparatus 8 and transmits the requested measurement order to the system control apparatus 8, and also receives the analysis result from the blood analyzing apparatus 5 and stores and manages the received analysis result.

<Operation of Sample Processing System in First Layout Example>

Hereinafter, an operation of the sample processing system 1 in the first layout example according to the present embodiment is described.

Figure 8:
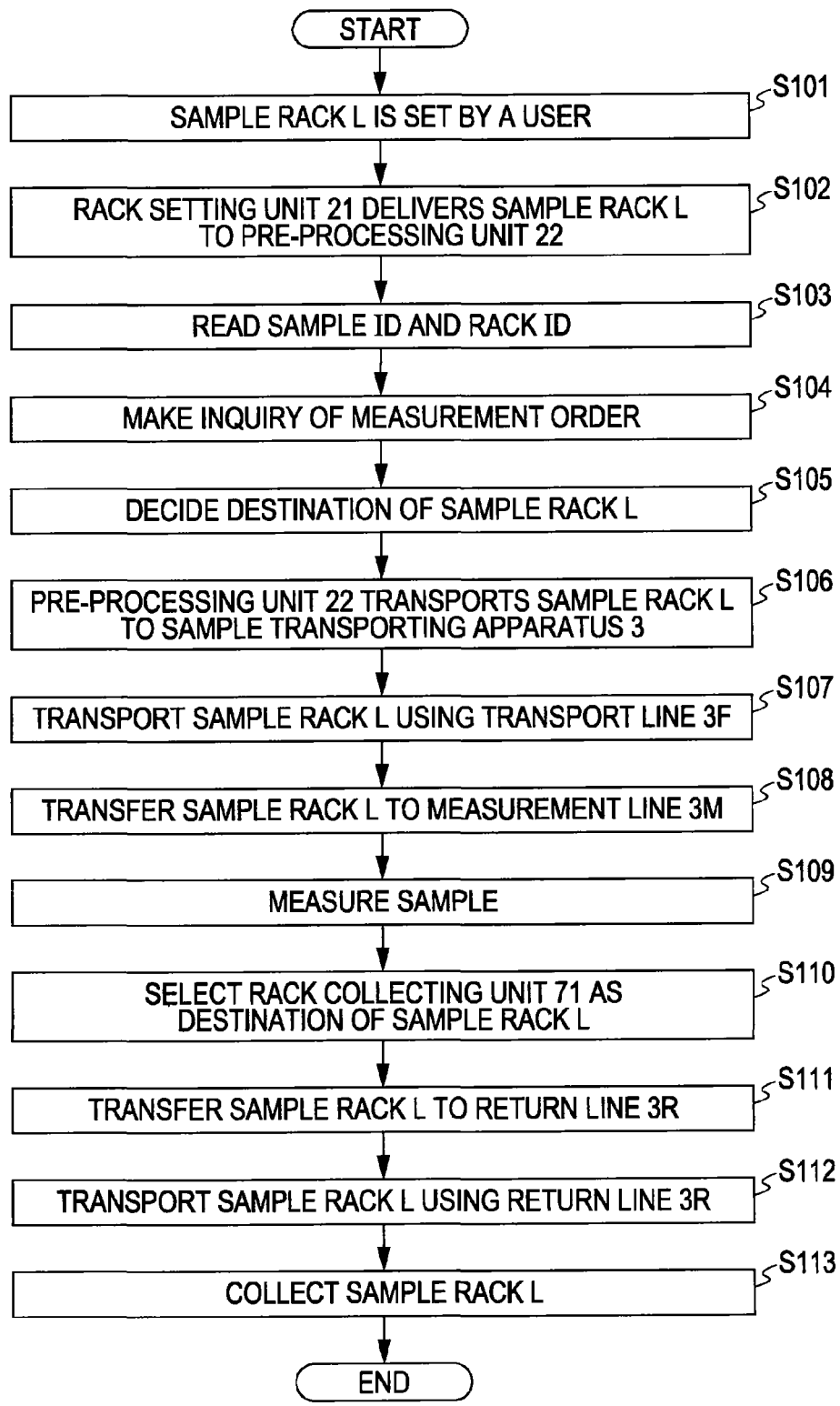
FIG. 8 is a flow chart illustrating an operation flow of the sample processing system in the first layout example according to the embodiment.
Figure 9:
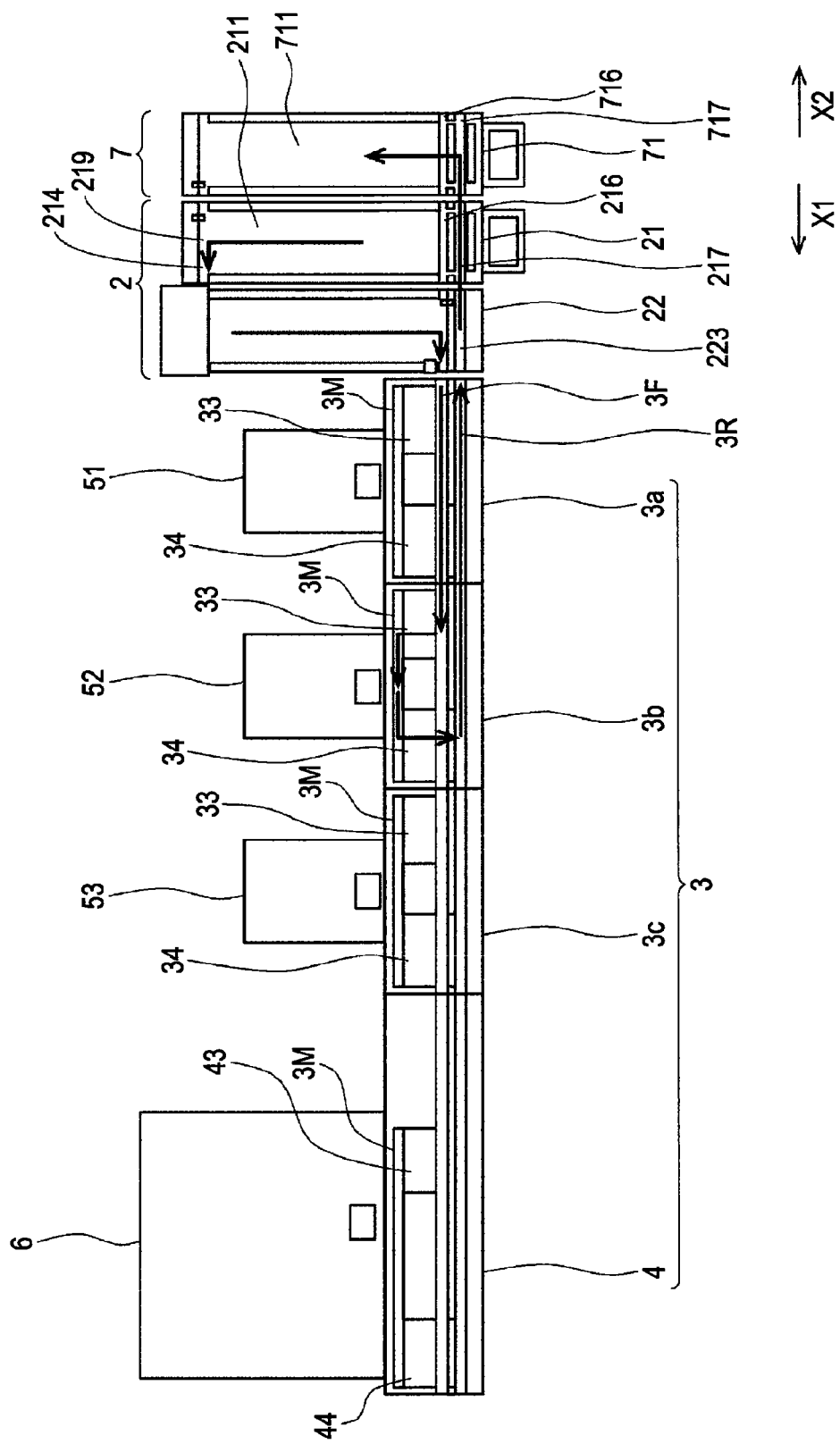
FIG. 9 is a schematic view for describing sample rack transport paths of the sample processing system in the first layout example according to the embodiment.

FIG. 8 is a flow chart illustrating an operation flow of the sample processing system 1 in the first layout example. FIG. 9 is a schematic view for describing the transport paths for transporting the sample rack L of the sample processing system 1 in the first layout example. The arrows illustrated in FIG. 9 denote the transport paths for transporting the sample rack L. As an initial step to start the sample processing by the sample processing system 1, an operator inputs an instruction to start the sample processing to the sample processing system 1 by manipulating an operation panel 21b of the rack setting unit 21. Then, the sample rack L is loaded in the rack setting unit 21 (step S101), and the sample rack L loaded in the rack loading section 211 is detected by the sensor 212, 213. The controller 21a drives the engagement portions 211a to transport the sample rack L backward to reach the rack delivering position 214, and further drives the protruding section 215 to deliver the sample rack L to the pre-processing unit 22 (step S102).

The sample rack L delivered from the rack delivering position 214 of the rack setting unit 21 is transported leftward toward the pre-processing unit 22 to arrive at the barcode reading position. As soon as the sample rack L arrives at the barcode reading position, the controller 22a of the pre-processing unit 22 controls the barcode reader 22b to read the sample ID of the sample container T held in the sample rack L and the rack ID of the sample rack L (S103).

The controller 22a then controls the engagement portions 221a to transfer the sample rack forward on the rack loading section 221 to the rack delivering position 222, and transmits the stored rack ID, holding position, and sample ID to the system control apparatus 8. The system control apparatus 8 which received the rack ID, holding position, and sample ID makes an inquiry of the measurement order to the test information management apparatus 9 (step S104), and stores the measurement order in association with the rack ID, holding position, and sample ID.

As soon as the sample rack L arrives at the rack delivering position 222, the controller 22a controls the barcode reader 222a to read the rack ID from the rack barcode of the sample rack L, and transmits a transport instruction request data including the read rack ID to the system control apparatus 8. After the system control apparatus 8 receives the transport instruction request data, the system control apparatus 8 searches the measurement order associated with the same rack ID in the hard disc to decide the destination of the sample rack L (step S105). In an example described below, the measurement unit 52 is selected as the destination of the sample rack L. The system control apparatus 8 transmits a transport instruction data for transporting the sample rack L to the decided destination to the pre-processing unit 22 and the sample transporting apparatus 3. After the controller 22a receives the transport instruction data, the controller 22a controls the protruding portion 225 to deliver the sample rack L leftward from the rack delivering position 222 (step S106).

The sample transporting apparatus 3 transports the sample rack L using the transport line 3F to the sample transport unit 3b corresponding to the measurement unit 52 which is the destination indicated by the transport instruction data (step S107). Thereafter, the sample rack L arrives at the sample transport unit 3b corresponding to the measurement unit 52 which is the destination. Then, the sample rack L in the sample transport unit 3b is transferred from the transport line 3F to the pre-analysis rack holding section 33 to be temporarily kept there. The sample rack L is transferred to the measurement line 3M (step S108), and the sample held in the sample rack L is then supplied to the measurement unit 52.

Then, the sample held in the sample rack L is measured by the measurement unit 52 (step S109). In the event that the destination is the smear preparation apparatus 6, a smear is prepared from the sample. The information processing unit 54 obtains an analysis result of the sample based on the measured data, and the analysis result is transmitted to the system control apparatus 8 and the test information management apparatus 9. After the sample processing is done, the sample transport unit 3b transports the sample rack L from the measurement line 3M to the post-analysis rack holding section 34 to temporarily keep the sample rack L there. The system control apparatus 8 selects the rack collecting unit 71 as the destination of the sample rack L (step S110), and transmits a transport instruction data indicating the destination thus selected to the sample transporting apparatus 3 and the sample collecting apparatus 7. The sample transporting apparatus 3 transfers the sample rack L to the return line 3R (step S111) to transport the sample rack L using the return line 3R (step S112).

The sample rack L transported by the return line 3R is guided to the second transport path 717 of the rack collecting unit 71 by way of the transport path 223 of the pre-processing unit 22 and the second transport path 217 of the rack setting unit 21, and then transferred from the second transport path 717 to the rack storing section 711 (step S113).

In the first layout example, the sample collecting apparatus 7 is provided next to the sample setting apparatus 2 so that the sample collecting apparatus 7 and the sample setting apparatus 2 are positioned on the right end of the whole structure of the sample processing system 1. According to the system layout, the operator can load and collect the sample rack L in one place. In some facilities, it may be necessary to load and collect the sample rack L on the right end of the entire sample processing system 1. In such a case, the sample processing system 1 in the first layout example is suitably used in the facilities.

Second Layout Example of Sample Processing System

Figure 10:
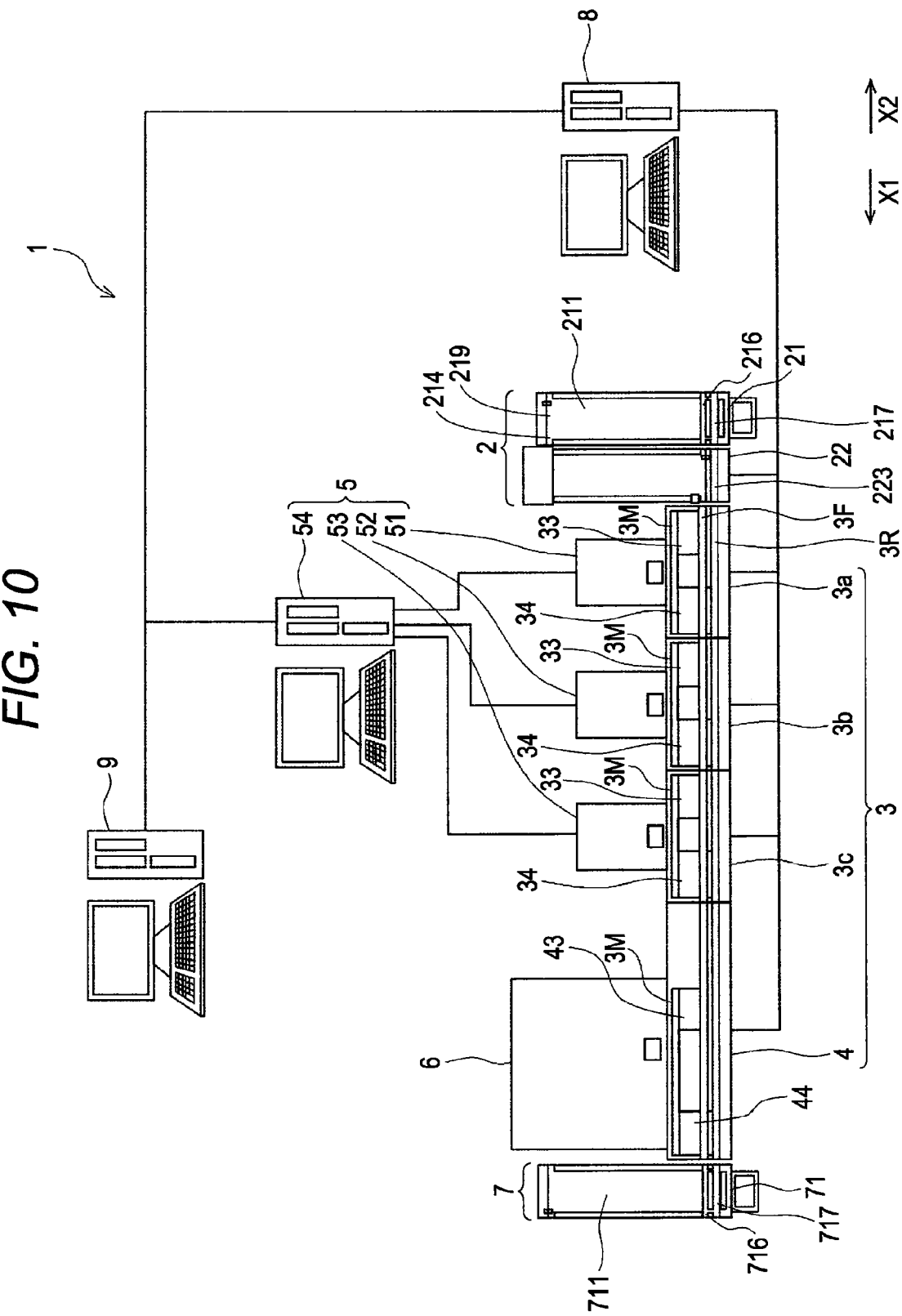
FIG. 10 is a schematic plan view illustrating an overall structure of a sample processing system in a second layout example according to the embodiment.

FIG. 10 is a schematic plan view illustrating an overall structure of a sample processing system in a second layout example according to the present embodiment. As illustrated in FIG. 10, in a sample processing system 1 in the second layout example, the sample collecting apparatus 7 is not provided next to the sample setting apparatus 2 but is connected to the left end of the sample transporting apparatus 3. The sample collecting apparatus 7 is positioned so that the transport line 3F of the sample transporting apparatus 3 and the first transport path 716 of the rack collecting unit 71 are linearly continuous, and the return line 3R of the sample transporting apparatus 3 and the second transport path 717 of the rack collecting unit 71 are linearly continuous.

<Operation of Sample Processing System in Second Layout Example>

Hereinafter, an operation of the sample processing system 1 in the second layout example according to the present embodiment is described.

Figure 11:
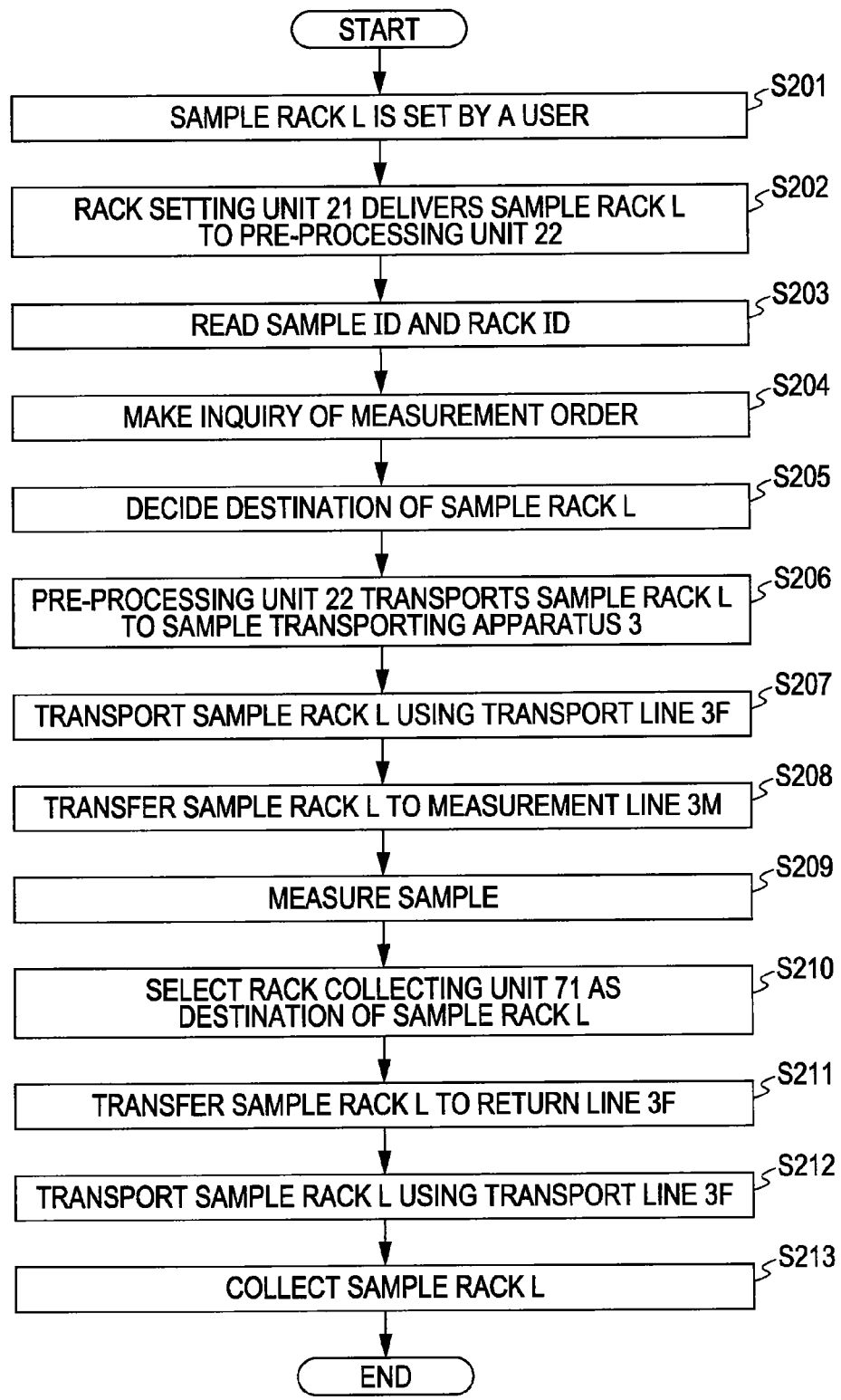
FIG. 11 is a flow chart illustrating an operation flow of the sample processing system in the second layout example according to the embodiment.
Figure 12:
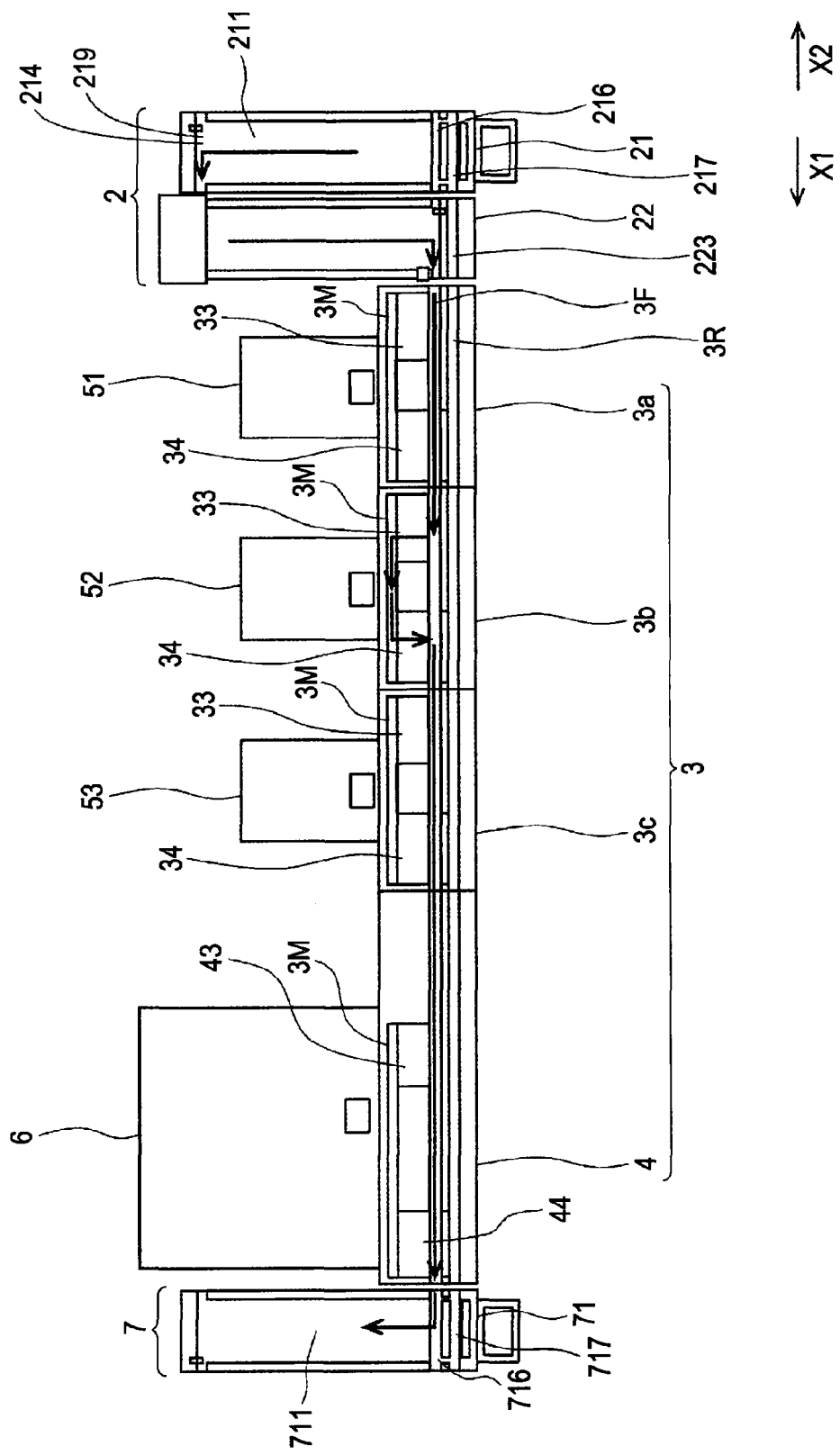
FIG. 12 is a schematic view for describing sample rack transport paths of the sample processing system in the second layout example according to the embodiment.

FIG. 11 is a flow chart illustrating an operation flow of the sample processing system 1 in the second layout example. FIG. 12 is a schematic view for describing the transport paths for transporting the sample rack L of the sample processing system 1 in the second layout example. In FIG. 11, processing steps of S201 to S210 are similar to the processing steps of S101 to S110 in the operation of the sample processing system 1 in the first layout example, and description of the similar processing steps is omitted.

The sample transporting apparatus 3 which received the transport instruction data indicating the rack collecting unit 71 as the destination transfers the sample rack L to the transport line 3F (step S211), and transports the sample rack L using the transport line 3F (step S212).

The sample rack L transported by the transport line 3F is guided to the first transport path 716 of the rack collecting unit 71 and then transferred from the first transport path 716 to the rack storing section 711 (step S213).

In the second layout example, the sample collecting apparatus 7 is connected to the left end of the sample transporting apparatus 3, and the sample collecting apparatus 7 and the sample setting apparatus 2 are separated from each other. According to the system layout, the operator can load the sample rack L at a position on the right end of the sample processing system 1, while collecting the sample rack L at a position on the left end of the sample processing system 1. In some facilities, it may be necessary to load the sample rack L on the right end of the entire sample processing system 1 and collect the sample rack L on the left end thereof. In such a case, the sample processing system 1 in the second layout example is suitably used in the facilities.

Third Layout Example of Sample Processing System

Figure 13:
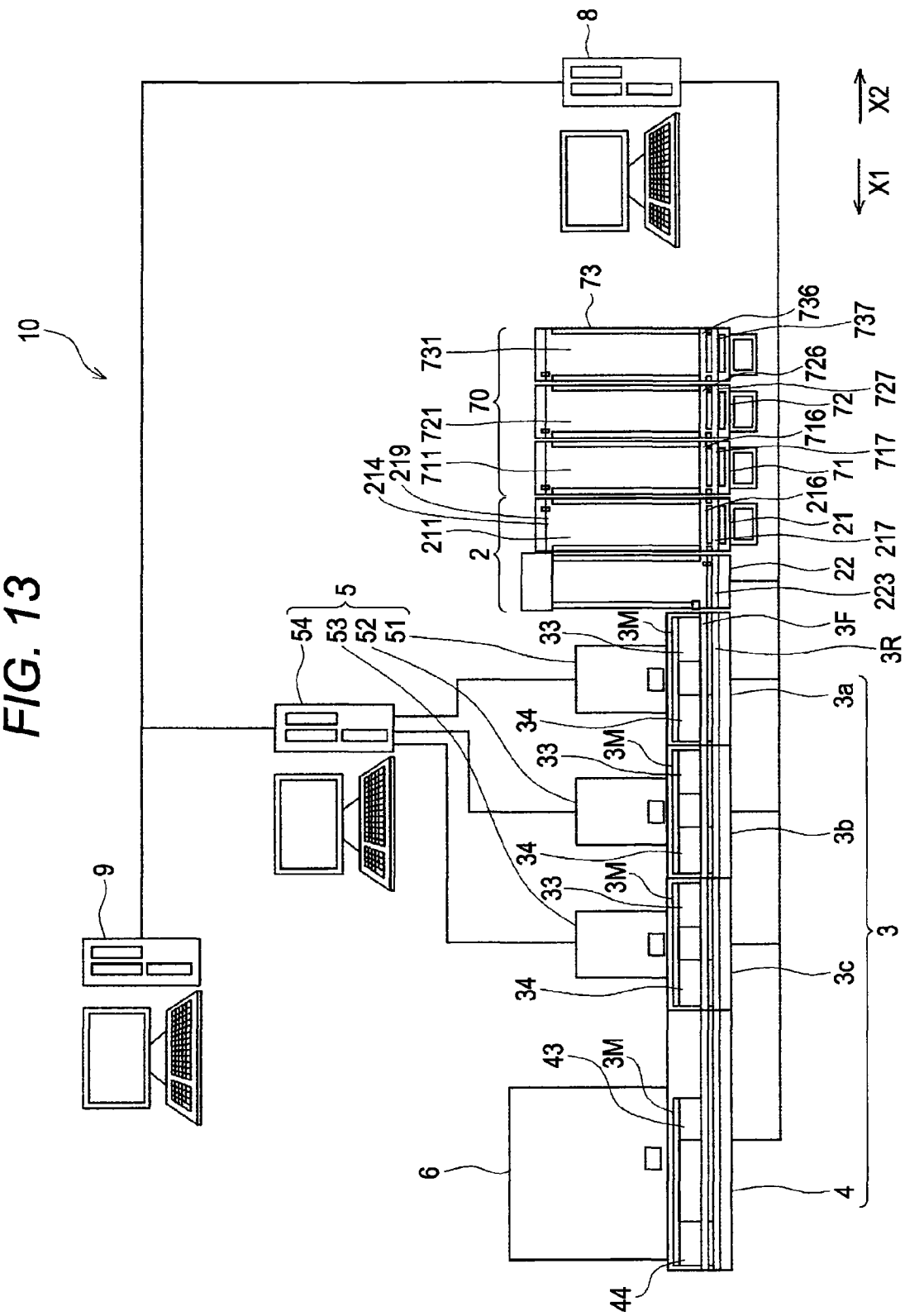
FIG. 13 is a schematic plan view illustrating an overall structure of a sample processing system in a third layout example according to the embodiment.

FIG. 13 is a schematic plan view illustrating an overall structure of a sample processing system in a third layout example according to the present embodiment. As illustrated in FIG. 13, in a sample processing system 10 in the third layout example, a sample collecting apparatus 70 has three rack collecting units 71, 72, and 73. The shared unit 20 is used in the rack collecting units 71, 72, and 73. All of the rack collecting units 71, 72, and 73 have an identical structure. The rack housing section 201 of the shared unit 20 used as the rack collecting unit 72 serves as a rack storing section 721 for storing therein the collected sample rack L. Similarly, the first transport path 206 and the second transport path 207 of the shared unit 20 used as the rack collecting unit 72 serve as a first transport path 726 and a second transport path 727. The rack housing section 201 of the shared unit 20 used as the rack collecting unit 73 serves as a rack storing section 731 for storing therein the collected sample rack L. The first transport path 206 and the second transport path 207 of the shared unit 20 serve as a first transport path 736 and a second transport path 737.

In the third layout example, the rack collecting apparatus 70 is connected to the right side of the rack setting unit 21. Of the rack collecting units 71, 72, and 73, the two rack collecting units adjacently disposed are connected to each other. The rack setting unit 21 and the rack collecting units 71, 72, and 73 are positioned so that the first transport path 216 of the rack setting unit 21 and the first transport paths, 716, 726, and 736 of the rack collecting units 71, 72, and 73 are linearly continuous, and the second transport path 217 of the rack setting unit 21 and the second transport paths, 717, 727, and 737 of the rack collecting units 71, 72, and 73 are linearly continuous.

<Operation of Sample Processing System in Third Layout Example>

Hereinafter, an operation of the sample processing system 10 in the third layout example according to the present embodiment is described.

Figure 14:
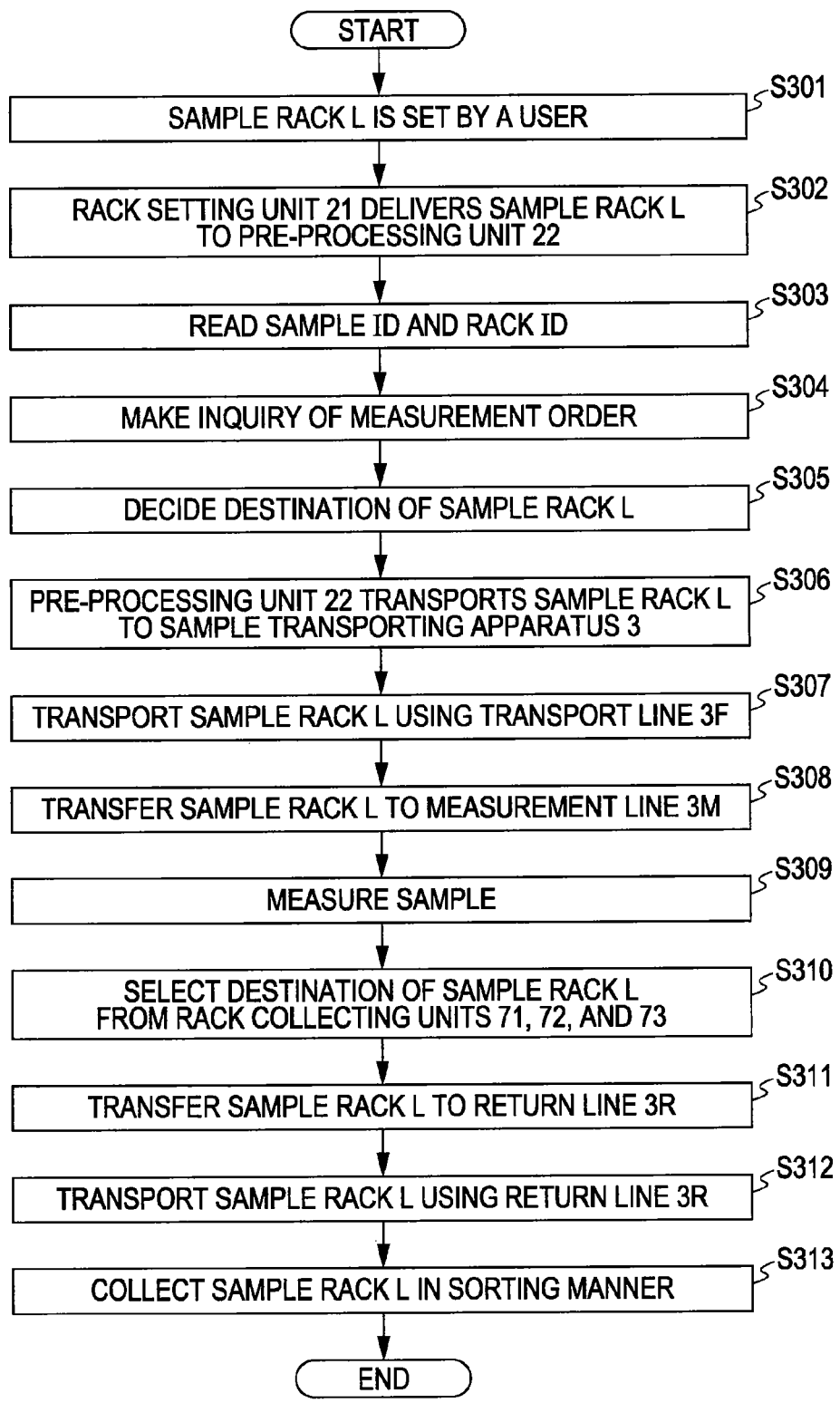
FIG. 14 is a flow chart illustrating an operation flow of the sample processing system in the third layout example according to the embodiment.
Figure 15:
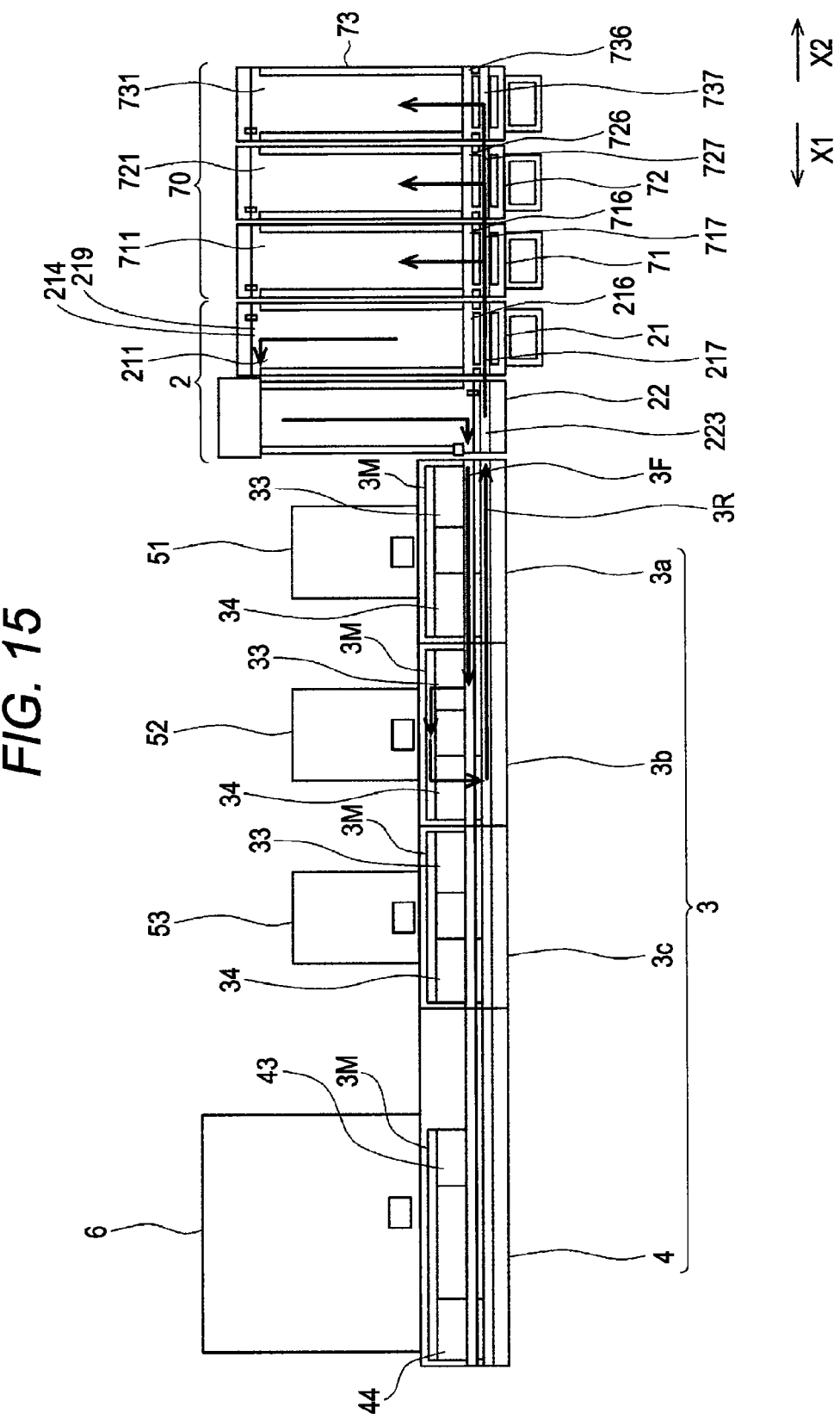
FIG. 15 is a schematic view for describing sample rack transport paths of the sample processing system in the third layout example according to the embodiment.

FIG. 14 is a flow chart illustrating an operation flow of the sample processing system 10 in the third layout example. FIG. 15 is a schematic view for describing the transport paths for transporting the sample rack L of the sample processing system 10 in the third layout example. In FIG. 14, processing steps of S301 to S309 are similar to the processing steps of S101 to S109 in the operation of the sample processing system 1 in the first layout example, and description of the similar processing steps is omitted.

The system control apparatus 8 which received the sample analysis result from the blood analyzing apparatus 5 decides the destination where the sample rack L holding the analyzed sample should be transported based on the received analysis result (step S310). In the process, the transport destination is selected from the rack collecting units 71, 72, and 73 based on different criteria. The transport destination is selected from the rack collecting units 71, 72, and 73 such that; the transport destination of the sample rack L which failed in the sample barcode read is the rack collecting unit 71, the transport destination of the sample rack L which holds any sample whose analysis result includes information suggesting retest of the sample is the rack collecting unit 72, and the transport destination of the sample rack L which succeeded in the sample barcode read and holds no sample to be retested is the rack collecting unit 73. The system control apparatus 8 transmits a transport instruction data indicating the decided destination to the sample transporting apparatus 3 and the sample collecting apparatus 70.

The sample transporting apparatus 3 transfers the sample rack L from the post-analysis rack holding section 34 to the return line 3R (step S311) to transport the sample rack L from the return line 3R (step S312). The sample rack L transported by the return line 3R is guided to the second transport path 717 of the rack collecting unit 71 by way of the transport path 223 of the pre-processing unit 22 and the second transport path 217 of the rack setting unit 21. The sample racks L are then collected by the rack collecting units 71, 72, and 73 in a sorting manner (step S313). More specifically, the sample rack L whose destination is the rack collecting unit 71 is transferred from the second transport path 717 of the rack collecting unit 71 to the rack storing section 711 and then collected by the rack collecting unit 71, the sample rack L whose destination is the rack collecting unit 72 is transferred from the second transport path 727 of the rack collecting unit 72 to the rack storing section 721 and then collected by the rack collecting unit 72, and the sample rack L whose destination is the rack collecting unit 73 is transferred from the second transport path 737 of the rack collecting unit 73 to the rack storing section 731 and then collected by the rack collecting unit 73.

In the third layout example, the sample collecting apparatus 70 is provided next to the sample setting apparatus 2 so that the sample collecting apparatus 70 and the sample setting apparatus 2 are positioned on the right end of the whole structure of the sample processing system 10. According to the system layout, the operator can load and collect the sample rack L in one place. In some facilities, it may be necessary to load and collect the sample rack L on the right end of the entire sample processing system 10. In such a case, the sample processing system 10 in the third layout example is suitably used in the facilities. Because a plurality of rack collecting units 71, 72, and 73 are provided in the sample collecting apparatus 70, the sample collecting apparatus 70 can more efficiently collect the sample rack L. Another advantage of the third layout example is to select which of the rack collecting units 71, 72, and 73 should collect the sample rack L. This advantage makes it unnecessary for the operator to manually sort out the collected sample racks to subject the samples to any subsequent processing steps, thus alleviating the operator's labor. For example, the samples collected by the rack collecting unit 71 can be handled accordingly to improve the readability of their sample barcodes such as replacement of the sample barcodes or removal of soil or dirt attached to the sample barcodes, and then loaded again in the sample processing system 1. The samples collected by the rack collecting unit 72 can be collectively retested later. The samples collected by the rack collecting unit 73 can be collectively preserved or disposed of.

Fourth Layout Example of Sample Processing System

Figure 16:
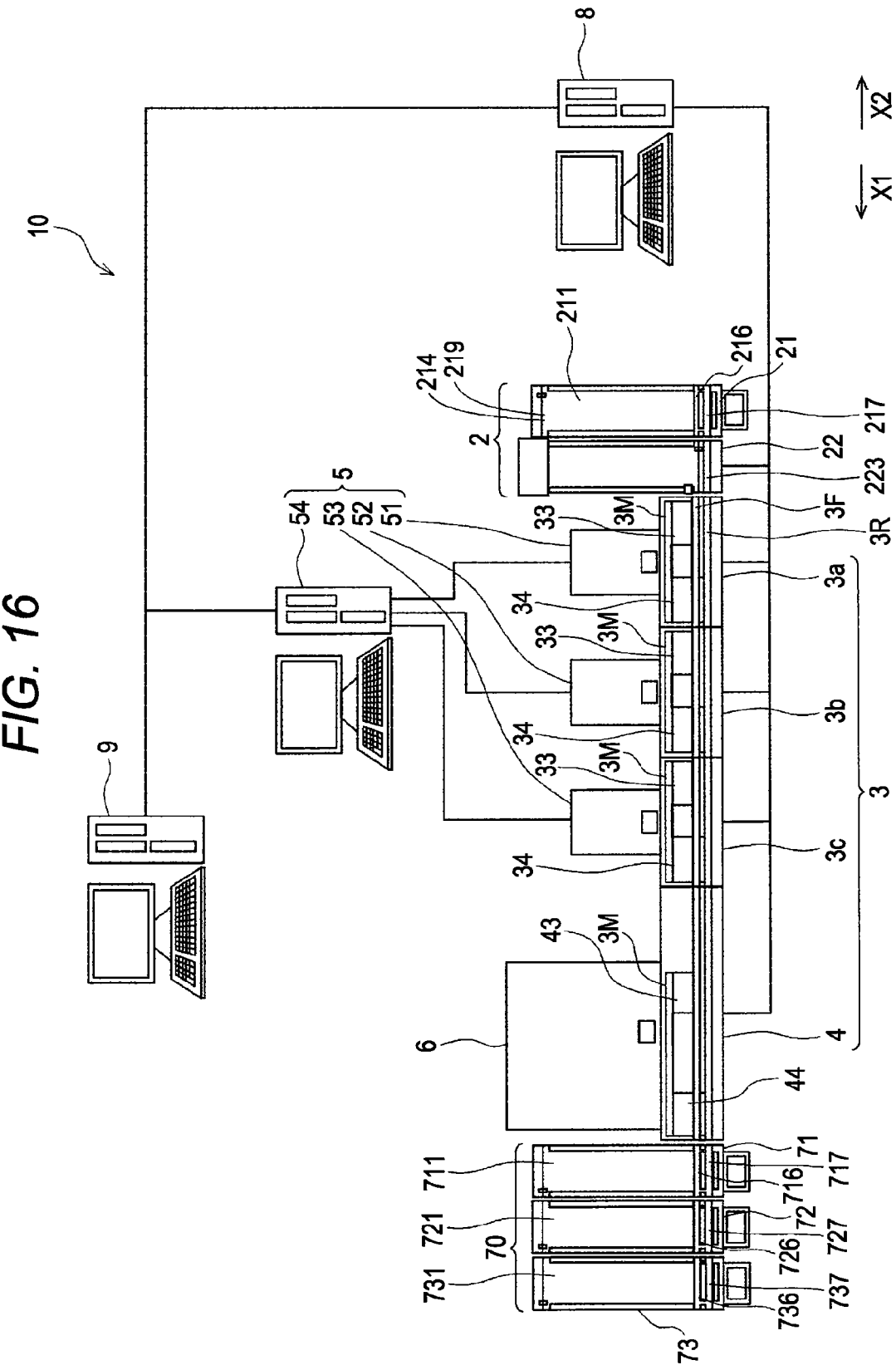
FIG. 16 is a schematic plan view illustrating an overall structure of a sample processing system in a fourth layout example according to the embodiment.

FIG. 16 is a schematic plan view illustrating an overall structure of a sample processing system in a fourth layout example according to the present embodiment. As illustrated in FIG. 16, in a sample processing system 10 in the fourth layout example, the sample collecting apparatus 70 is not provided next to the sample setting apparatus 2 but is connected to the left end of the sample transporting apparatus 3. The sample collecting apparatus 70 is positioned so that the transport line 3F of the sample transporting apparatus 3 and the first transport paths 716, 726, and 736 of the rack collecting units 71, 72, and 73 are linearly continuous, and the return line 3R of the sample transporting apparatus 3 and the second transport paths 717, 727, and 737 of the rack collecting units 71, 72, and 73 are linearly continuous.

<Operation of Sample Processing System in Fourth Layout Example>

Hereinafter, an operation of the sample processing system 10 in the fourth layout example according to the present embodiment is described.

Figure 17:
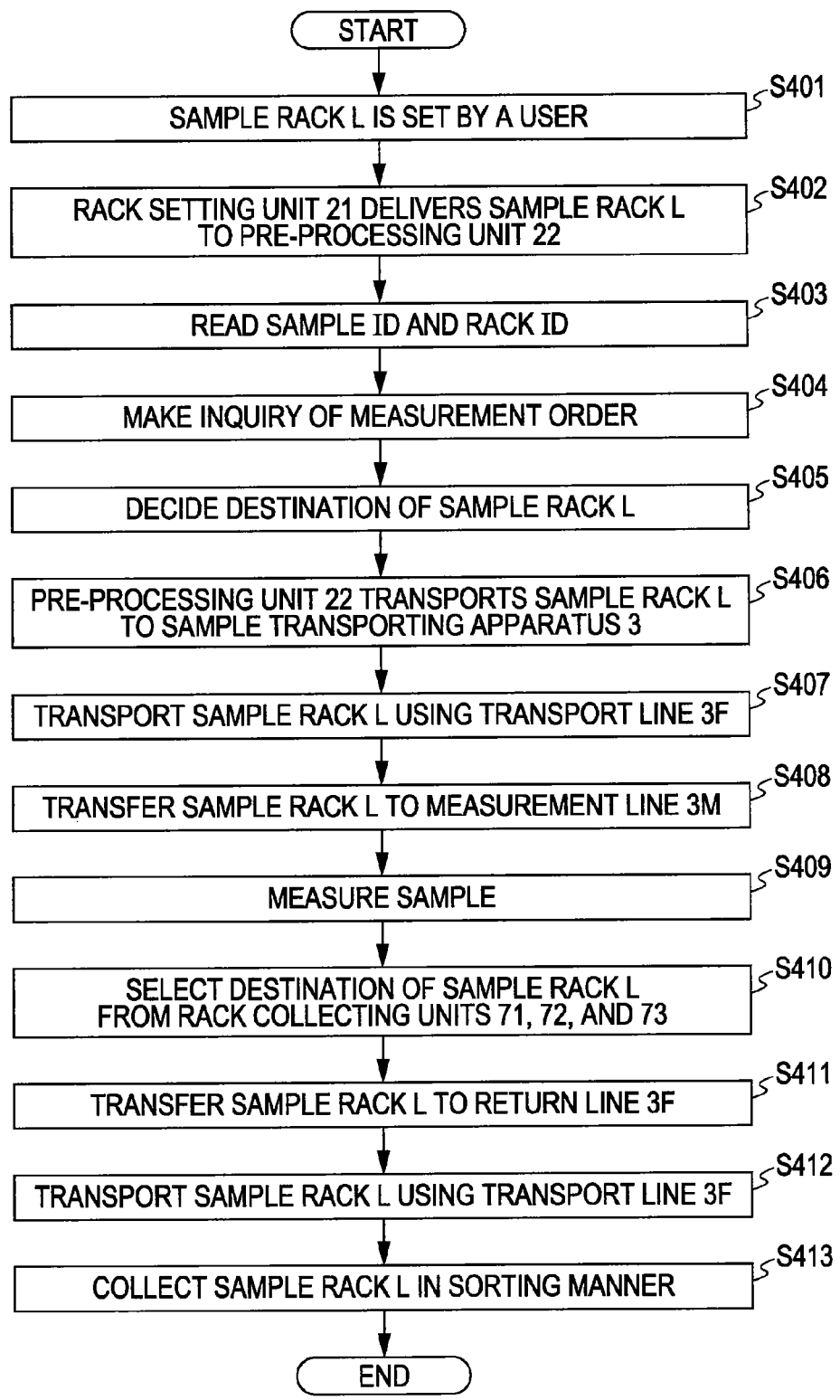
FIG. 17 is a flow chart illustrating an operation flow of the sample processing system in the fourth layout example according to the embodiment.
Figure 18:
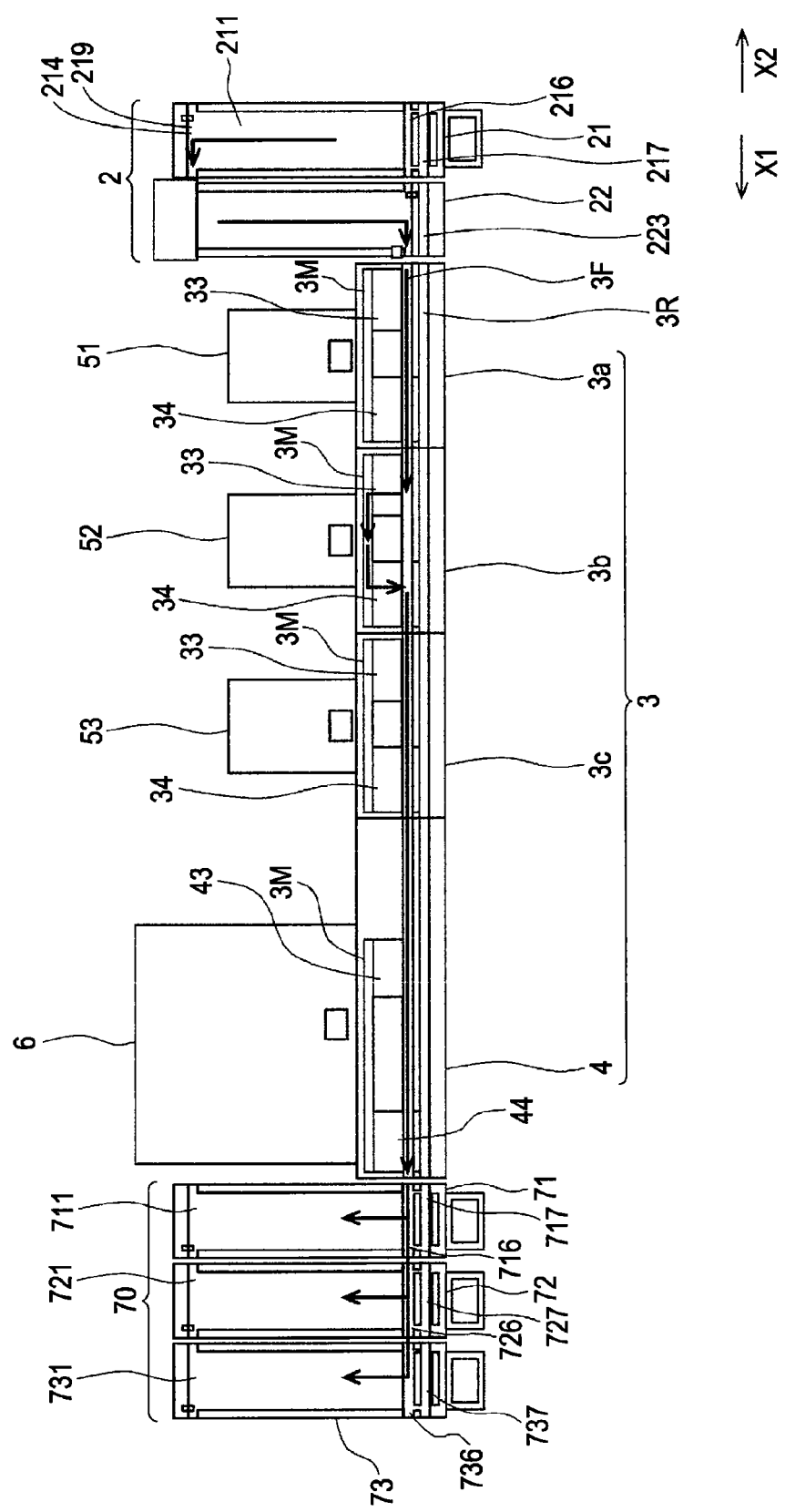
FIG. 18 is a schematic view for describing sample rack transport paths of the sample processing system in the fourth layout example according to the embodiment.

FIG. 17 is a flow chart illustrating an operation flow of the sample processing system 10 in the fourth layout example. FIG. 18 is a schematic view for describing the transport paths for transporting the sample rack L of the sample processing system 10 in the fourth layout example. In FIG. 17, processing steps of S401 to S412 are similar to the processing steps of S201 to S212 in the operation of the sample processing system 1 in the second layout example, and description of the similar processing steps is omitted. To decide the destination in step S410, the transport destination is selected from the rack collecting units 71, 72, and 73 based on given criteria in a manner similar to the third layout example.

The sample rack L transported on the transport line 3F is guided to the first transport path 716 of the rack collecting unit 71. The sample racks L are then collected by the rack collecting units 71, 72, and 73 in a sorting manner (step S413). More specifically, the sample rack L whose destination is the rack collecting unit 71 is transferred from the first transport path 716 of the rack collecting unit 71 to the rack storing section 711 and then collected by the rack collecting unit 71, the sample rack L whose destination is the rack collecting unit 72 is transferred from the first transport path 726 of the rack collecting unit 72 to the rack storing section 721 and then collected by the rack collecting unit 72, and the sample rack L whose destination is the rack collecting unit 73 is transferred from the second transport path 736 of the rack collecting unit 73 to the rack storing section 731 and then collected by the rack collecting unit 73.

In the fourth layout example, the sample collecting apparatus 70 is connected to the left end of the sample transporting apparatus 3, and the sample collecting apparatus 70 and the sample setting apparatus 2 are separated from each other. According to the system layout, the operator can load the sample rack L at a position on the right end of the sample processing system 10, while collecting the sample rack L at a position on the left end of the sample processing system 10. In some facilities, it may be necessary to load the sample rack L on the right end of the entire sample processing system 10 and collect the sample rack L on the left end thereof. In such a case, the sample processing system 10 in the fourth layout example is suitably used in the facilities. Because a plurality of rack collecting units 71, 72, and 73 are provided in the sample collecting apparatus 70, the sample collecting apparatus 70 can more efficiently collect the sample rack L. Another advantage of the fourth layout example is to select which of the rack collecting units 71, 72, and 73 should collect the sample rack L. This advantage makes it unnecessary for the operator to manually sort out the collected sample racks to subject the samples to any subsequent processing steps, thus alleviating the operator's labor.

Fifth Layout Example of Sample Processing System

Figure 19:
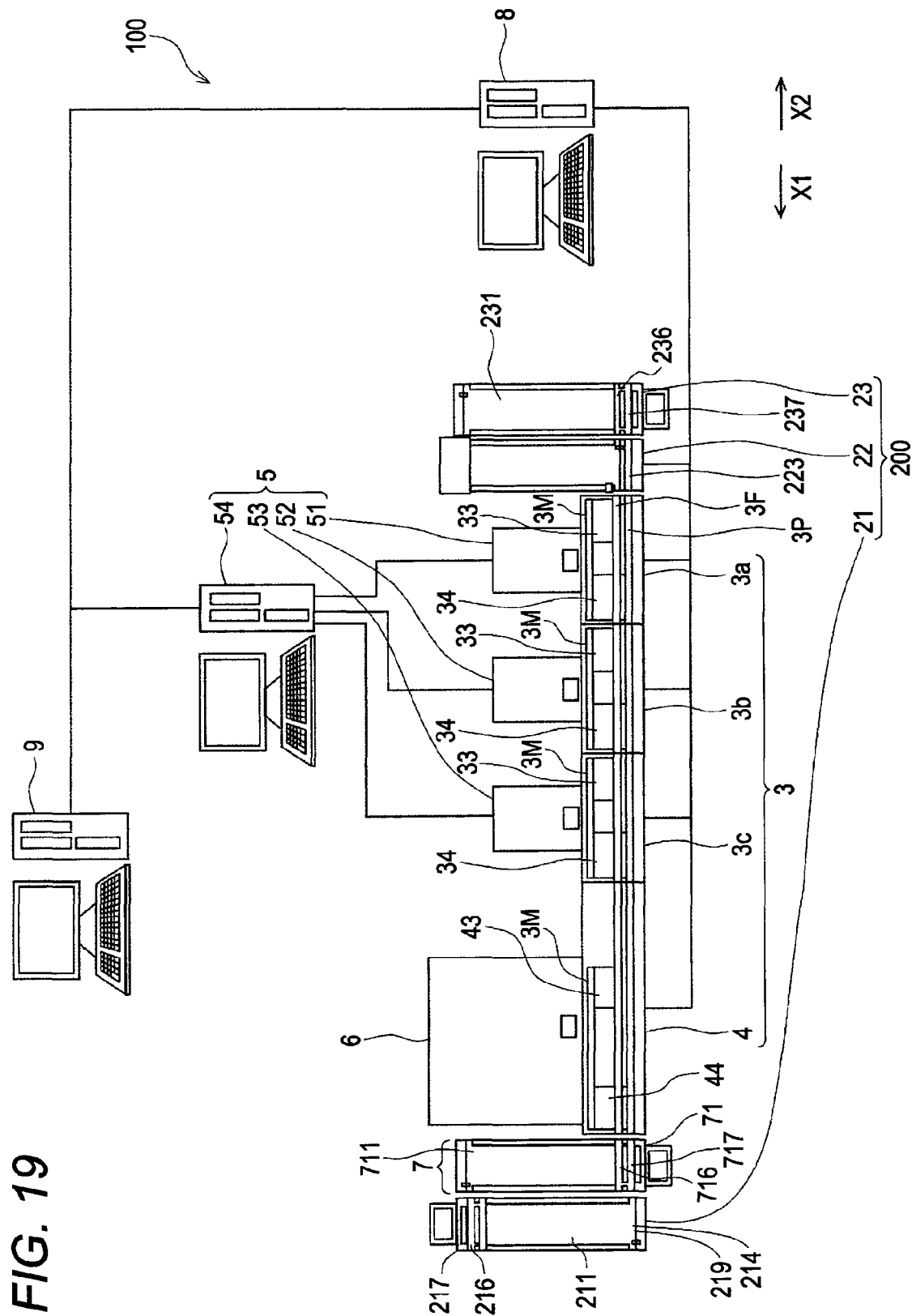
FIG. 19 is a schematic plan view illustrating an overall structure of a sample processing system in a fifth layout example according to the embodiment.

FIG. 19 is a schematic plan view illustrating an overall structure of a sample processing system in a fifth layout example according to the present embodiment. As illustrated in FIG. 19, in a sample processing system 100 in the fifth layout example, a sample setting apparatus 200 has a relay unit 23 in addition to the rack setting unit 21 and the pre-processing unit 22. In the fifth layout example, the sample collecting apparatus 7 provided with the rack collecting unit 71 is connected to the left end of the sample transporting apparatus 3, the rack setting unit 21 is separated from the pre-processing unit 22 and positioned on the left side of the rack collecting unit 71 such that the front and back of the rack setting unit 21 are reversed to the rack collecting unit 71. Specifically, the rack setting unit 21 is positioned so that the rack delivering position 214 (see FIG. 2) is located on the front side, and the first transport path 216 and the second transport path 217 are located on the rear side.

The relay unit 23 is provided on the right side of the pre-processing unit 22 connected to the right end of the sample transporting apparatus 3. The shared unit 20 is used as the relay unit 23. The rack housing section 201 of the shared unit 20 used as the relay unit 23 serves as a rack transferring section 231 for transferring the sample rack L. Similarly, the first transport path 206 and the second transport path 207 of the shared unit 20 used as the relay unit 23 respectively serve as a first transport path 236 and a second transport path 237.

In the sample processing system 100 in the fifth layout example, the return line 3R of the sample transporting apparatus 3 in the first layout example serves as a transport line 3P for transporting the sample rack L loaded in the rack setting unit 21 to the pre-processing unit 22 and the relay unit 23. In the sample processing system 100 in the fifth layout example, the rack setting unit 21, the rack collecting unit 71, the sample transporting apparatus 3, the pre-processing unit 22, and the relay unit 23 are positioned so that the first transport path 716 of the rack collecting unit 71, the transport line 3F of the sample transporting apparatus 3, the rack delivering position 222 of the pre-processing unit 22 (see FIG. 2), and the first transport path 236 of the relay unit 23 are linearly continuous, and the rack delivering position 214 of the rack setting unit 21 (see FIG. 2), the second transport path 717 of the rack collecting unit 71, the transport line 3P of the sample transporting apparatus 3, the transport path 223 of the pre-processing unit 22, and the second transport path 237 of the relay unit 23 are linearly continuous. Further, the sample rack L can be transported to the pre-processing unit 22 from a rack delivering position on the rearmost side of the rack transferring section 231 of the relay unit 23 (corresponding to the rack delivering position 204 of the shared unit 20 (see FIG. 5A)).

<Operation of Sample Processing System in Fifth Layout Example>

Hereinafter, an operation of the sample processing system 100 in the fifth layout example according to the present embodiment is described.

Figure 20A:
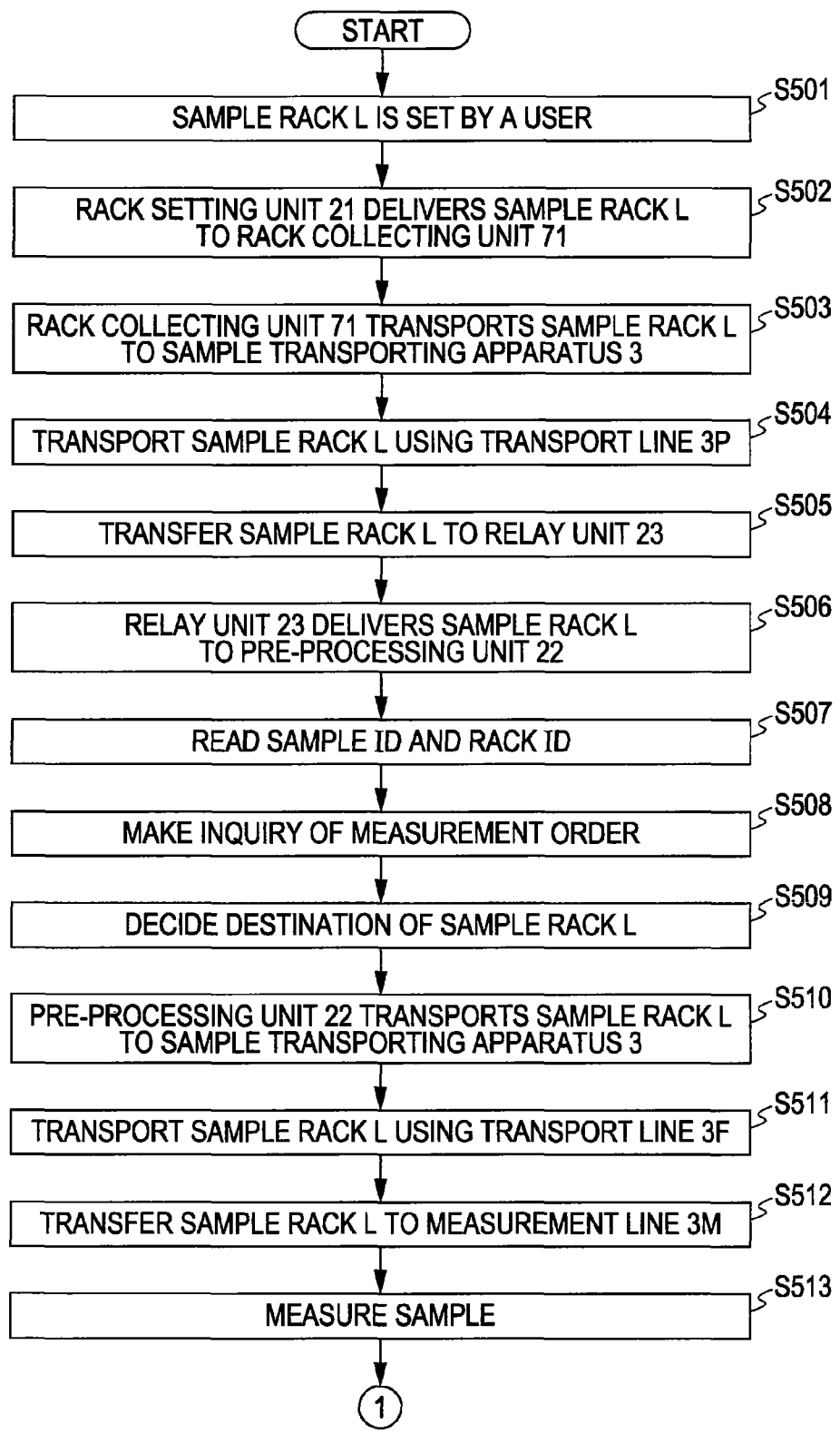
FIG. 20A a flow chart (first half) illustrating an operation flow of the sample processing system in the fifth layout example according to the embodiment.
Figure 20B:
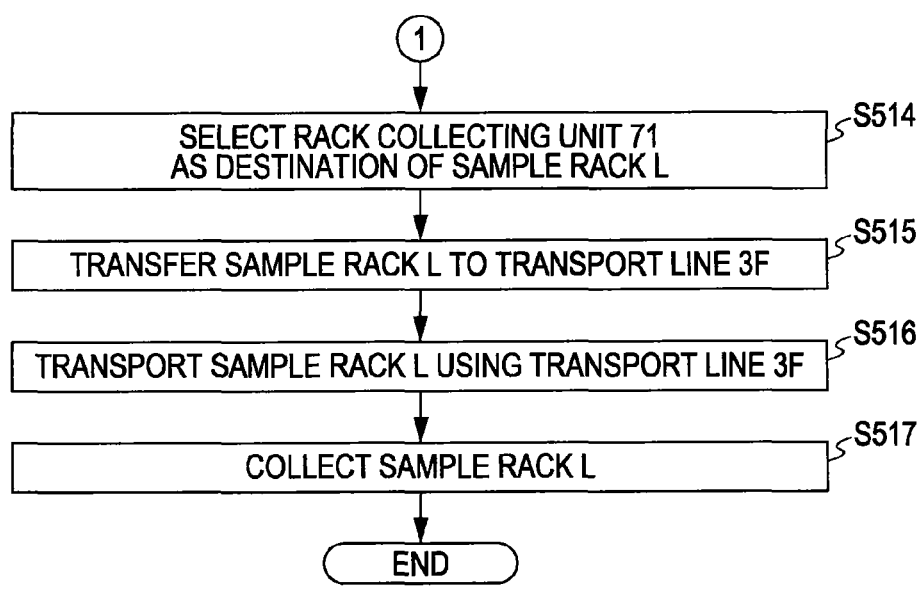
FIG. 20B is a flow chart (latter half) illustrating the operation flow of the sample processing system in the fifth layout example according to the embodiment.

FIG. 20A and FIG. 20B are flow charts illustrating an operation flow of the sample processing system 100 in the fifth layout example. FIG. 21 is a schematic view for describing the transport paths for transporting the sample rack L of the sample processing system 100 in the fifth layout example. When the sample rack L is loaded in the rack setting unit 21 after an instruction to start the sample processing is received by the sample processing system 100 (step S501), the sample rack L loaded in the rack loading section 211 is detected by the sensor 212, 213. The controller 21a drives the engagement portions 211a to transport the sample rack L forward to arrive at the rack delivering position 214, and further drives the protruding section 215 to transfer the sample rack L to the second transport path 717 of the rack collecting unit 71 (step S502). The sample rack L is transferred from the second transport path 717 of the rack collecting unit 71 to the transport line 3P of the sample transporting apparatus 3 (step S503), and further transported rightward by the transport line 3P (step S504). The sample rack L transported on the transport line 3P is transferred to the second transport path 237 of the relay unit 23 by way of the transport path 223 of the pre-processing unit 22 (step S505).

The relay unit 23 transfers the sample rack L on the second transport path 237 to a rack delivering position through the rack transferring section 231, and further transfers the sample rack L leftward using a protruding portion (corresponding to the protruding portion 205 of the shared unit 20) to deliver the sample rack L to the pre-processing unit 22 (step S506). The processing steps of S507 to S517 are similar to the processing steps of S203 to S213 in the operation of the sample processing system 1 in the second layout example, and description of the similar processing steps is omitted.

In the fifth layout example, the sample collecting apparatus 7 is connected to the left end of the sample transporting apparatus 3, and the rack setting unit 21 of the sample setting apparatus 200 is provided on the left side of the sample collecting apparatus 7. According to the system layout, the operator can load and collect the sample rack L in one place. In some facilities, it may be necessary to load and collect the sample rack L on the left end of the entire sample processing system 100. In such a case, the sample processing system 100 in the fifth layout example is suitably used in the facilities.

According to the present embodiment, the rack collecting unit 71 is provided with the first transport path 716 for transporting the sample rack in the direction of X1, the second transport path 717 for transporting the sample rack in the direction of X2, the rack storing section 711 for storing therein the sample rack, and the rack transferring section 718 for transferring the sample rack from the first transport path 716 and the second transport path 717 to the rack storing section 711. In the first and third layout examples, the second transport path 717 serves to receive the sample rack from the second transport path 217 of the rack setting unit 21 provided on the left side of the rack collecting unit 71. In the fifth layout example, the second transport path 717 serves to receive the sample rack from the third transport path 219 of the rack setting unit 21 provided on the left side of the rack collecting unit 71. In the second and fourth layout examples, the first transport path 716 serves to receive the sample rack from the transport line 3F of the sample transporting apparatus 3 provided on the right side of the rack collecting unit 71. Therefore, the rack collecting unit 71 can be located at a position near the sample setting apparatus 2, 200 (first layout example, third layout example, and fifth layout example), or the rack collecting unit 71 can be located at a position distant from the sample setting apparatus 2 (second layout example and fourth layout example).

In the first and third layout examples, the second transport path 717 serves to receive the sample rack from the side of the sample transporting apparatus 3 provided on the left side of the rack collecting unit 71. In the second, fourth and fifth layout examples, the first transport path 716 serves to receive the sample rack from the side of the sample transporting apparatus 3 provided on the right side of the rack collecting unit 71. Therefore, the rack collecting unit 71 can be located on the right side of the sample transporting apparatus 3 (first layout example and third layout example), or the rack collecting unit 71 can be located on the left side of the sample transporting apparatus 3 (second layout example, fourth layout example, and fifth layout example). As described so far, the sample processing system according to the present embodiment can improve the degree of freedom in the layout of the structural elements provided therein as compared with the prior art.

In the present embodiment, the second transport path 717 of the rack collecting unit 71 can transport the sample rack not only in the direction of X2 but also in the direction of X1. In the case where the rack collecting unit 71 is provided on the left side of the sample transporting apparatus 3 as illustrated in the second, fourth and fifth layout examples, therefore, the sample rack transported from the sample transporting apparatus 3 can be transported into the rack collecting unit 71 by the second transport path 717. Accordingly, the sample rack holding the sample already measured by, for example, the measurement unit 51 is transported not on the transport line 3F but on the return line 3R, and the sample rack thus transported can be more smoothly collected by the rack collecting unit 71.

In the present embodiment, the rack collecting unit 71 can carry the sample rack stored in the rack storing section 711 out of the rack collecting unit 71 using the third transport path 719. In the case where the rack collecting unit 71 is used as the rack setting unit 21 in the first, second, third and fourth layout examples, and as the relay unit 23 in the fifth layout example, the third transport path 719 serves to transport the sample rack to the side of the pre-processing unit 22. In the case where the rack collecting unit 71 is used as the rack setting unit 21 in the fifth layout example, the third transport path 719 serves to transport the sample rack to the second transport path 717 of the rack collecting unit 71. Thus, the rack collecting unit 71 can be used as the rack setting unit 21 and the relay unit 23. This makes it unnecessary to develop and design the rack collecting unit 71, rack setting unit 21, and relay unit 23 separately, thereby reducing production steps in the development of the sample processing system as compared with the prior art.

In the present embodiment, the rack collecting unit 71 is equipped with the engagement portions 711a for delivering the sample rack from the rack storing section 711 to the rack delivering position (corresponding to the rack delivering position 204). Therefore, it is unnecessary to use the rack transferring section 718 to deliver the sample rack L stored in the rack storing section 711 to the rack delivering position. According to the structural advantage, the rack transferring section 718 can be solely used to transfer the sample rack to the rack storing section 711. This accelerates the transport of the sample rack on the first transport path 716 and the second transport path 717 to the rack storing section 711.

According to the present embodiment, the first transport path 716 and the second transport path 717 of the rack collecting unit 71 are provided on one end side of the rack storing section 711. The location of these transport paths can restrict the transferring direction of the sample rack by the rack transferring section 718 to one direction only (backward), helping the mechanism of the rack transferring section 718 be simplified.

In the sample processing system according to the present embodiment, the first transport path 716 of the rack collecting unit 71 can transport the sample rack in the direction of X1 to move the sample rack out of the rack collecting unit 71, and the second transport path 717 of the rack collecting unit 71 can transport the sample rack in the direction of X2 to move the sample rack out of the rack collecting unit 71. In the third layout example, the second transport path 717 of the rack collecting unit 71 serves to transport the sample rack to the second transport path 727 of the rack collecting unit 72 adjacent thereto. In the fourth layout example, the first transport path 716 of the rack collecting unit 71 serves to transport the sample rack to the second transport path 727 of the rack collecting unit 72 adjacent thereto. Therefore, the sample collecting apparatus may include a plurality of rack collecting units regardless of whether the sample collecting apparatus is provided on the right side or left side of the sample transporting apparatus 3. Thus, a sample collecting apparatus having multiple stages can be provided (third layout example and fourth layout example). As a result, the overall performance of the sample processing system in collecting the sample rack L can be readily improved. In other words, a larger number of the sample racks L can be easily loaded in the system at a time. By simply increasing the number of the shared units 20 serving as the rack collecting unit, the performance of the sample collecting apparatus in collecting the sample rack can be improved.

In the present embodiment, the rack setting unit 21 is provided with the second transport path 217 which can transport the sample rack received from outside of the rack setting unit 21 in the direction of X2 to move the sample rack out of the rack setting unit 21, the third transport path 219 which can transport the sample rack from the rack delivering position 214 in the direction of X1, the rack loading section 211 where the sample rack can be loaded, and the engagement portions 211a which can transport the sample rack loaded in the rack loading section 211 to the rack delivering position 214. In the first to fourth layout examples, the third transport path 219 serves to transport the sample rack to the side of the pre-processing unit 22 provided on the left side of the rack setting unit 21. In the fifth layout example, the third transport path 219 serves to transport the sample rack to the side of the sample transporting apparatus 3 provided on the right side of the rack setting unit 21. In the first and third layout examples, the second transport path 217 serves to transport the sample rack to the second transport path 717 of the rack collecting unit 71 provided on the right side of the rack setting unit 21. Therefore, the rack setting unit 21 can be provided on the right side of the sample transporting apparatus 3 (on the right side of the pre-processing unit 22) (first to fourth layout examples), the rack setting unit 21 with its front and back reversed can be provided on the left side of the sample transporting apparatus 3 (fifth layout example), or the rack collecting unit 71 can be provided on the right side of the rack setting unit 21 (first and third layout examples). As described so far, the sample processing system according to the present embodiment can improve the degree of freedom in the layout of the structural elements provided therein as compared with the prior art.

In the present embodiment, the rack setting unit 21 is provided with the first transport path 216 which can transport the sample rack received from outside of the rack setting unit 21 in the direction of X1 to move the sample rack out of the rack setting unit 21, and the rack transferring section 218 which transfers the sample rack from the first transport path 216 and the second transport path 217 to the rack loading section 211. In the case where the rack setting unit 21 is used as the rack collecting unit 71 in the second, fourth and fifth layout examples, the first transport path 216 serves to receive the sample rack from the sample transporting apparatus 3. In the case where the rack setting unit 21 is used as the rack collecting unit 71 in the first and third layout examples, the second transport path 217 serves to receive the sample rack from the side of the sample transporting apparatus 3. Thus, the rack setting unit 21 can be used as the rack collecting unit 71. This makes it unnecessary to develop and design the rack collecting unit 71 and the rack setting unit 21 separately, thereby reducing production steps in the development of the sample processing system as compared with the prior art.

Other Embodiments

In the embodiment described so far, the sample setting apparatus 2 includes the rack setting unit 21 and the pre-processing unit 22 which can be connected to each other. The present invention, however, is not necessarily limited thereto. The sample setting apparatus may be a single unit integrally formed.

The embodiment described so far illustrates the example in which one rack setting unit 21 is provided in the sample processing system. The present invention, however, is not necessarily limited thereto. A plurality of rack setting units 21 may be provided.

In the embodiment described so far, the sample ID is read from the sample barcode and the rack ID is read from the rack barcode as a step before the sample processing by the pre-processing unit 22. The present invention, however, is not necessarily limited thereto. In place of reading the sample ID and the rack ID from the barcodes, information including the sample ID and the rack ID may be stored in and read from a wireless tag. In place of or in addition to reading the sample ID and the rack ID, detection of a sample volume, detection of whether the blood sample includes coagulation, or detection of chyle concentration in the blood sample, for example, may be performed before the sample processing.

In the embodiment described so far, the sample racks L are collected by the three rack collecting units 71, 72, and 73 in a sorting manner in the third and fourth layout examples. The present invention, however, is not necessarily limited thereto. Alternatively, one of the rack collecting units may be chosen and solely used to collect the sample rack L, to use the other rack collecting units to collect the sample rack L after a given number of sample racks L (for example, maximum number of loadable sample racks L in the rack collecting unit) is collected by the rack collecting unit of the first choice.

In the embodiment described so far, the measurement line 3M is used as the transport path for supplying the sample to the measurement units, however, the transport line 3F may be used as the transport path for supplying the sample to the measurement units.

In the embodiment described so far, the third transport path 209 of the shared unit 20 pushes the sample rack using the protruding portion 205 to carry the sample rack out of the shared unit 20. The present invention, however, is not necessarily limited thereto. A belt conveyer may be used as the third transport path 209 in a manner similar to the first transport path 206 and the second transport path 207.

In the embodiment described so far, the sample processing system 1 is provided with the hemocyte analyzing apparatus 5 which classifies the hemocytes included in the sample into different types and counts the hemocytes by each type. The present invention, however, is not necessarily limited thereto. The sample processing system may be equipped with a sample analyzing apparatus other than the hemocyte analyzing apparatus, such as immunoassay apparatus, blood coagulation measuring apparatus, biochemical analyzing apparatus, or urine analyzing apparatus, wherein a sample such as blood or urine is transported to a measurement unit of the sample analyzing apparatus.

In the embodiment described so far, the blood analyzing apparatus 5 has the three measurement units 51, 52, and 53, and the information processing unit 54. The present invention, however, is not necessarily limited thereto. The measurement unit may be provided singularly or plurally. The measurement unit and the information processing unit may be integrally formed. It is not necessarily the case that the information processing unit 54 controls the operations of the measurement units 51, 52, and 53. Each of the measurement units may be equipped with a controller including a CPU and a memory, wherein the controllers control the measurement units, and the information processing unit processes measured data obtained by the measurement units to generate a sample analysis result.

What is claimed is:

1. A rack collecting unit, comprising:
a first transport path;
a second transport path arranged in parallel with the first transport path;
a storing section configured to store therein a sample rack;
a side wall that surrounds the storing section, the first transport path and the second transport path, wherein the side wall comprises:
a first side;
a second side that is opposite to the first side;
a first opening defined in the first side of the side wall at one end side of the first transport path;
a second opening defined in the second side of the side wall at the other end side of the first transport path, wherein the first transport path extends between the first and second openings of the side wall;
a third opening defined in the first side of the side wall at one end side of the second transport path;
a fourth opening defined in the second side of the side wall at the other end side of the second transport path, wherein the second transport path extends between the third and fourth openings of the side wall;
a first conveyer configured to transport a sample rack carried onto the first transport path through the first opening, in a first direction, toward the second opening;
a first stopper located at the other end side of the first transport path and that prevents the sample rack on the first transport path from passing through the second opening;
a second conveyer configured to transport a sample rack carried onto the second transport path through the fourth opening, in a second direction opposite to the first direction, toward the third opening;
a second stopper located at the one end side of the second transport path and that prevents the sample rack on the second transport path from passing through the third opening; and a transferring section configured to transfer the sample rack carried onto the first transport path to the storing section in the case that the sample rack is carried onto the first transport path, wherein the transferring section is configured to transfer the sample rack carried onto the second transport path to the storing section in the case that the sample rack is carried onto the second transport path.

2. The rack collecting unit of claim 1, further comprising a third transport path for transporting the sample rack stored in the storing section outside of the rack collecting unit.

3. The rack collecting unit of claim 2, further comprising a rack feeding section configured to feed the sample rack from the storing section to the third transport path.

4. The rack collecting unit of claim 1, wherein the first transport path and the second transport path are provided on one end side of the rack collecting unit.

5. The rack collecting unit of claim 2, wherein the first transport path and the second transport path are provided on one end side of the rack collecting unit; and the third transport path is provided on the other end side of the rack collecting unit.

6. The rack collecting unit of claim 1, wherein the second conveyer is capable of transporting the sample rack in the first direction and the second direction.

7. The rack collecting unit of claim 1, wherein the transferring section transfers the sample rack in a direction orthogonal to the transport directions of the sample rack transported by the first conveyer and the second conveyer.

8. The rack collecting unit of claim 1, wherein an upper surface of the storing section, an upper surface of the first transport path, and an upper surface of the second transport path are formed in a substantially equal height; and the transferring section is configured to slide the sample rack on the first transport path and the second transport path toward the storing section.

9. A sample processing apparatus, comprising:
a rack setting unit, on which a sample rack holding a sample container is set by a user, and which sends out the sample rack;
a transport unit having one end side connected to the rack setting unit, the transport unit including a first transport line for transporting the sample rack sent out from the rack setting unit in a first direction, and a second transport line for transporting a sample rack in a second direction opposite to the first direction;
a sample processing unit for processing a sample in the sampler container held by the sample rack transported by the first transport line of the transport unit; and
a rack collecting unit for collecting the sample rack transported by the transport unit,
wherein the rack collecting unit comprises:
  a first transport path connectable to the first transport line;
  a second transport path arranged in parallel with the first transport path and connectable to the second transport line;
  a storing section configured to store therein a sample rack;
  a side wall that surrounds the storing section, the first transport path and the second transport path, wherein the side wall comprises:
    a first side;
    a second side that is opposite to the first side;
    a first opening defined in the first side of the side wall at one end side of the first transport path;
    a second opening defined in the second side of the side wall at the other end side of the first transport path, wherein the first transport path extends between the first and second openings of the side wall;
    a third opening defined in the first side of the side wall at one end side of the second transport path, wherein the second transport path extends between the third and fourth openings of the side wall;
    a fourth opening defined in the second side of the side wall at the other end side of the second transport path;
  a first conveyer configured to transport a sample rack carried onto the first transport path through the first opening, in a first direction, toward the second opening;
  a first stopper located at the other end side of the first transport path and that prevents the sample rack on the first transport path from passing through the second opening;
  a second conveyer configured to transport a sample rack carried onto the second transport path through the fourth opening, in a second direction opposite to the first direction, toward the third opening;
  a second stopper located at the one end side of the second transport path and that prevents the sample rack on the second transport path from passing through the third opening; and
  a transferring section for transferring the sample rack carried onto the first transport path to the storing section in the case that the sample rack is carried onto the first transport path,
wherein the transferring section is configured to transfer the sample rack carried onto the second transport path to the storing section in the case that the sample rack is carried onto the second transport path,
and wherein the rack collecting unit is connectable to the other end side of the transport unit and the rack setting unit.

10. The sample processing apparatus of claim 9, further comprising
a second rack collecting unit having a structure identical to the rack collecting unit, wherein
the rack collecting unit and the second rack collecting unit are connectable to each other so that the first transport path of the rack collecting unit and a first transport path of the second rack collecting unit are continuous, and the second transport path of the rack collecting unit and a second transport path of the second rack collecting unit are continuous.

11. The sample processing apparatus of claim 9, wherein the rack setting unit has a structure identical to the rack collecting unit.

12. The sample processing apparatus of claim 9, wherein the rack collecting unit comprises a third transport path for transporting the sample rack stored in the storing section outside of the rack collecting unit.

13. The sample processing apparatus of claim 12, wherein the rack collecting unit comprises a rack feeding section configured to feed the sample rack from the storing section to the third transport path.

14. The sample processing apparatus of claim 9, wherein the first transport path and the second transport path are provided on one end side of the rack collecting unit.

15. The sample processing apparatus of claim 12, wherein the first transport path and the second transport path are provided on one end side of the rack collecting unit; and the third transport path is provided on the other end side of the rack collecting unit.

16. The sample processing apparatus of claim 9, wherein the second conveyer is capable of transporting the sample rack in the first direction and the second direction.

\* \* \* \* \*